United States Patent
Singh et al.

(10) Patent No.: US 10,640,830 B2
(45) Date of Patent: May 5, 2020

(54) DRUG SELECTION FOR NON-SMALL CELL LUNG CANCER THERAPY

(71) Applicant: NESTEC S.A., Vevey (CH)

(72) Inventors: Sharat Singh, Rancho Santa Fe, CA (US); Phillip Kim, Irvine, CA (US); Steven Lockton, San Diego, CA (US)

(73) Assignee: Société des Produits Nestlé S.A., Vevey (CH)

( * ) Notice: Subject to any disclaimer, the term of this patent is extended or adjusted under 35 U.S.C. 154(b) by 0 days.

(21) Appl. No.: 14/812,979

(22) Filed: Jul. 29, 2015

(65) Prior Publication Data
US 2016/0032403 A1    Feb. 4, 2016

Related U.S. Application Data

(63) Continuation of application No. PCT/IB2014/058790, filed on Feb. 4, 2014.

(60) Provisional application No. 61/761,105, filed on Feb. 5, 2013.

(51) Int. Cl.
*C12Q 1/6886*    (2018.01)
*G01N 33/574*    (2006.01)

(52) U.S. Cl.
CPC ........ *C12Q 1/6886* (2013.01); *G01N 33/5748* (2013.01); *G01N 33/57423* (2013.01); *C12Q 2600/106* (2013.01); *C12Q 2600/118* (2013.01); *C12Q 2600/156* (2013.01); *C12Q 2600/158* (2013.01); *G01N 2333/71* (2013.01); *G01N 2333/82* (2013.01); *G01N 2800/52* (2013.01)

(58) Field of Classification Search
CPC ..................................................... C12Q 1/6886
USPC ..................................................... 424/133.1
See application file for complete search history.

(56) References Cited

FOREIGN PATENT DOCUMENTS

| WO | 2011/008990 A1 | 1/2011 |
| WO | 2012/088337 A1 | 6/2012 |
| WO | 2012/119113 A2 | 9/2012 |

OTHER PUBLICATIONS

Pal et al (Mol Cancer Ther, 2010, 9(7): 1931-1944).*
Engelman et al (Science, 2007, 316(5827): 1039-1043).*
Yano et al (Cancer Research, 2008, 68(22): 9479-9487).*
McDermott et al (Cancer Res, 2010, 70(4): 1625-1634).*
Kim et al (Proteome Sci, 2011, 9(75): 1-15).*
Hoe, N. et al., "Selection of targeted agent(s) based on matching differential protein expression and mutational profile in NSCLC patients," Journal of Clinical Oncology, 29(15 Suppl):e21085, 2011.
Gong, H. et al., "Signatures of drug sensitivity in nonsmall cell lung cancer," International Journal of Proteomics, 2011:1-13, 2011.

* cited by examiner

*Primary Examiner* — Sean E Aeder
(74) *Attorney, Agent, or Firm* — Kilpatrick Townsend & Stockton LLP

(57) ABSTRACT

The present invention provides methods for selecting a suitable anticancer drug for the treatment of patient with non-small cell lung cancer (NSCLC). The present invention also provides methods for determining drug resistance in NSCLC patients receiving EGFR inhibitor therapy.

19 Claims, 13 Drawing Sheets

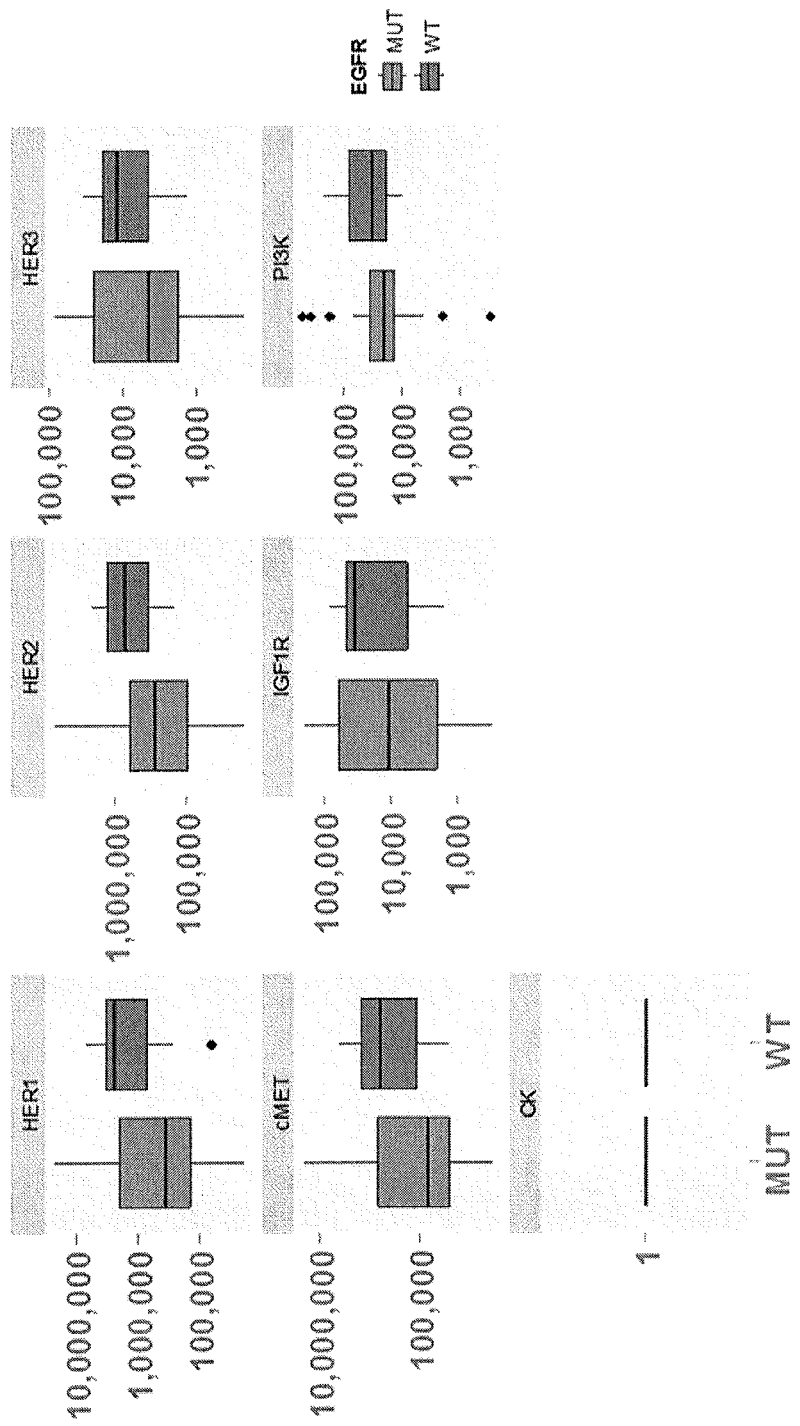

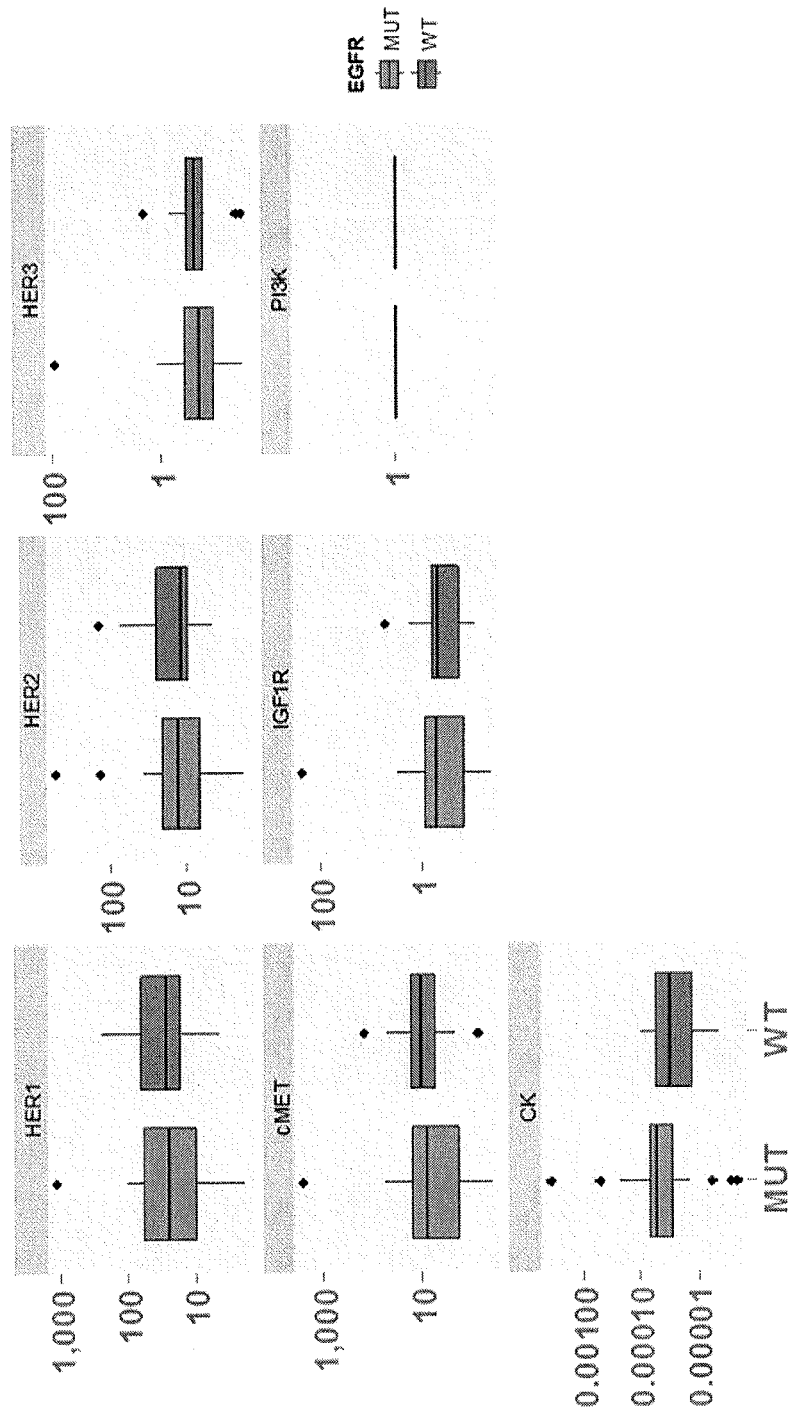

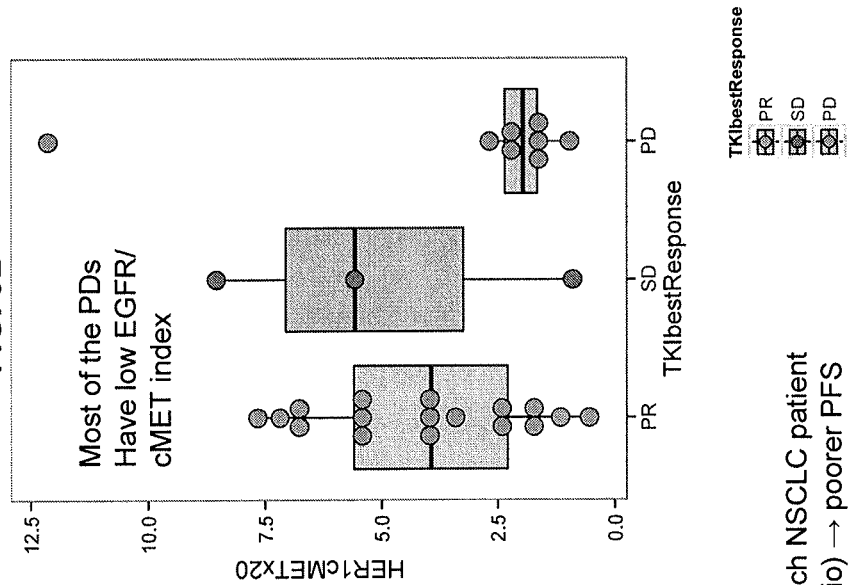
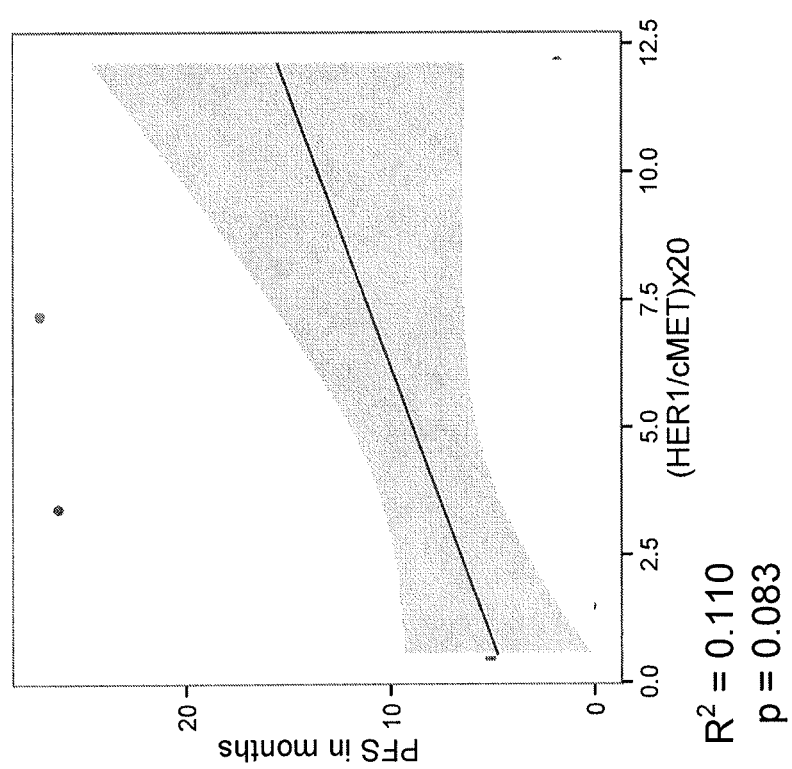

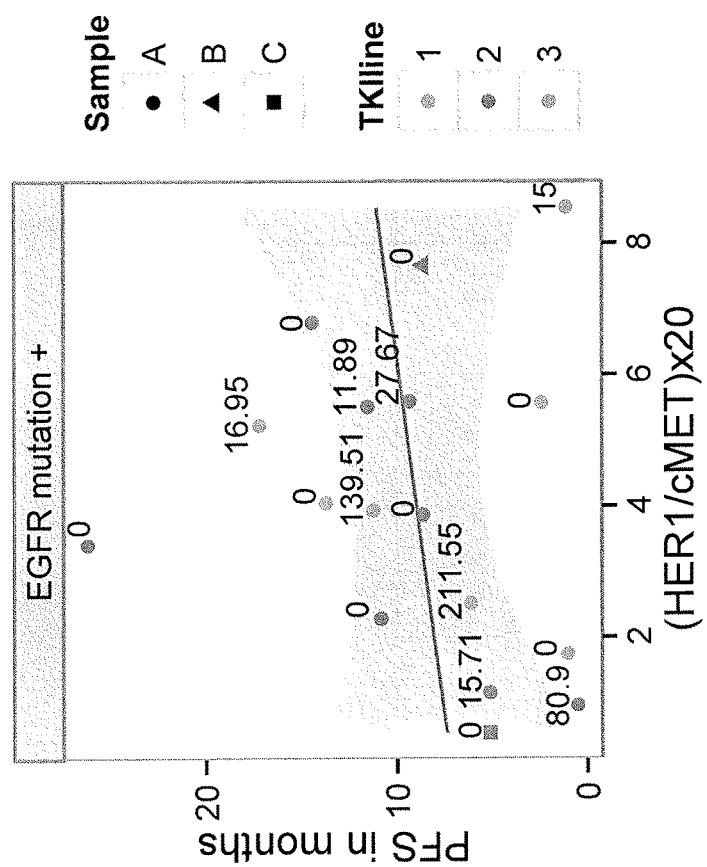
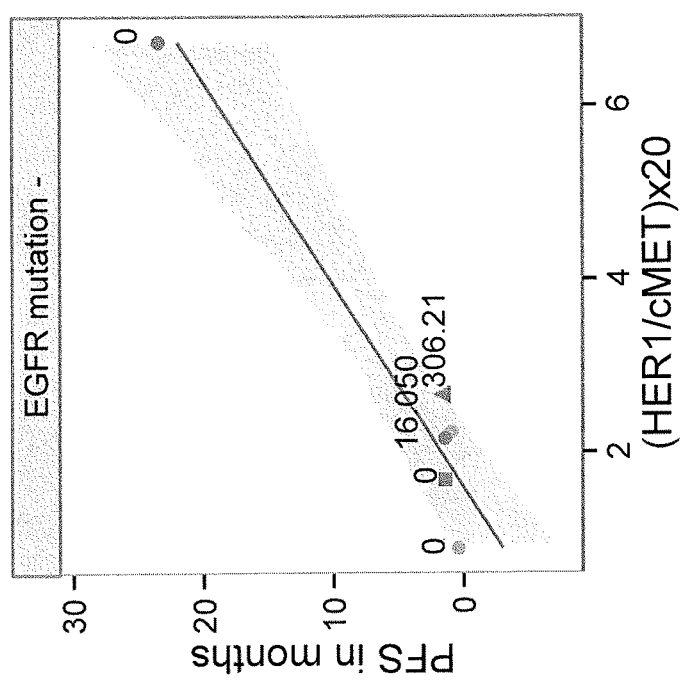
Correlative plot between PFS vs. relative (EGFR/cMET) level in each NSCLC patient segregated by EGFR mutation status

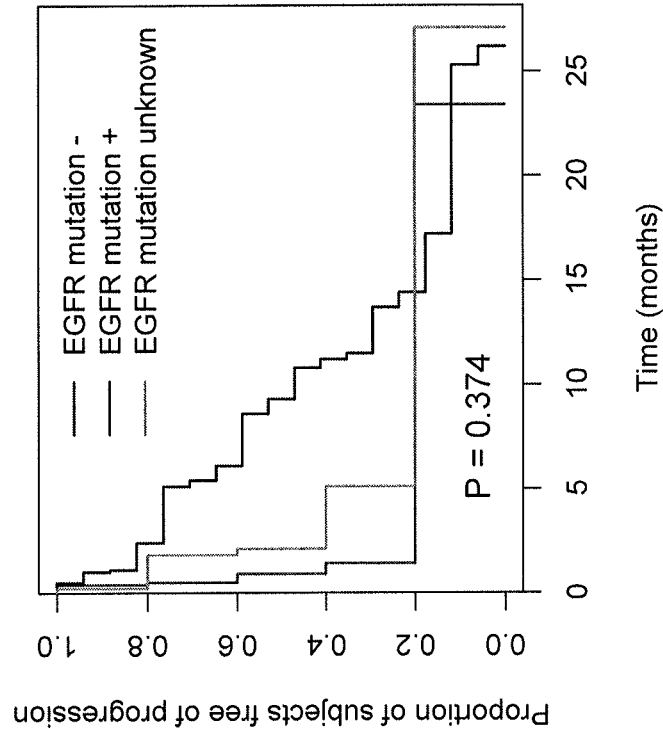
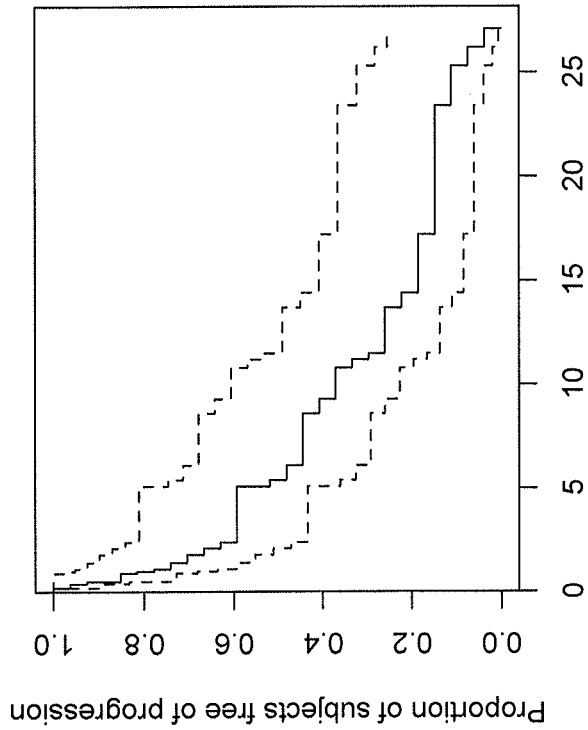
Kaplan Meier Curves on PFS
FIG. 5A All Subjects
FIG. 5B Stratified by EGFR mutation
Kaplan Meier based on mutation status
- EGFR mutant pts have better PFS consistent with literature

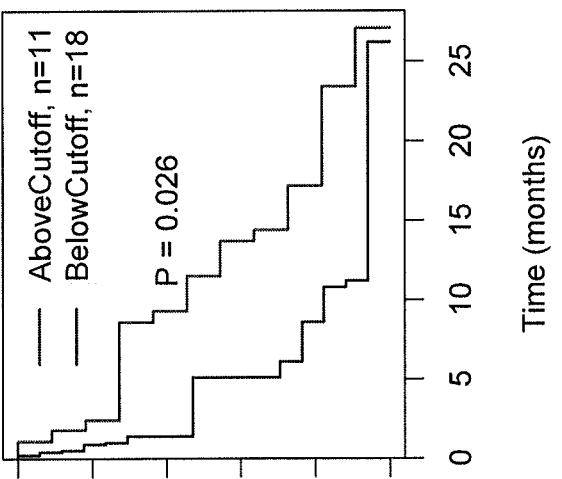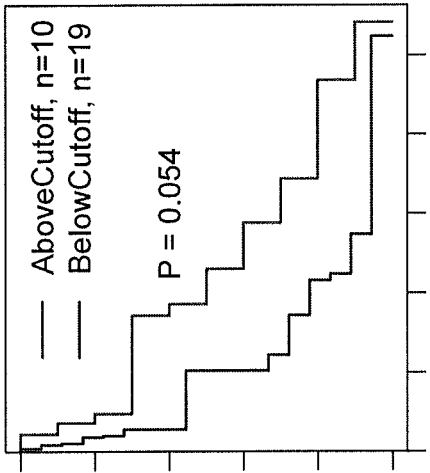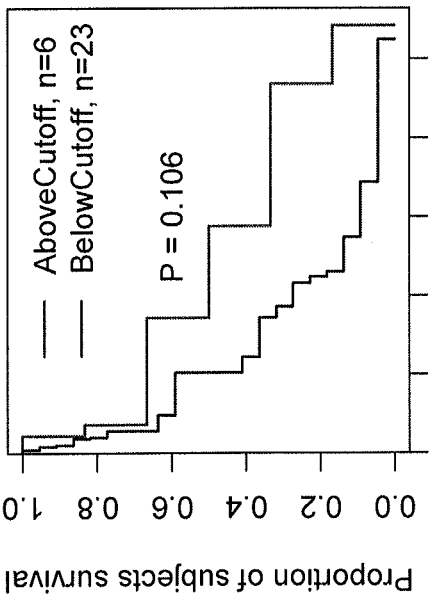
FIG. 6A Ratio cutoff = 6
FIG. 6B Ratio cutoff = 5
FIG. 6C Ratio cutoff = 4
All subjects, PFS & EGFR:cMET Index
EGFR/cMET ratio > 2 (or 20X to 120X higher EGFR level) showed EGFR inhibitor treatment benefit with statistical significance

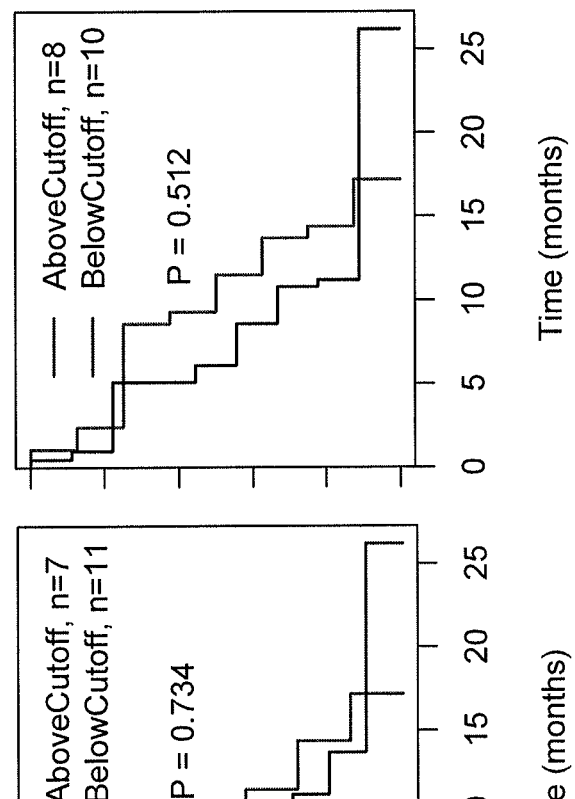

EGFR mut only, PFS & HER1:cMET x 20 ratio

Ratio cutoff = 3

Ratio cutoff = 2

Ratio cutoff = 1

EGFR/cMET ratio > 1 (or 20X to 60X higher EGFR level) showed EGFR inhibitor treatment benefit with statistical significance for EGFR mutant patients.

EGFR/cMET Index is predictive in both EGFR mutant patients as well as WT patients

Correlative plot between PFS vs. relative (HER1/cMET) level in each NSCLC patient
- as relative cMET level increases (reduction of HER1/cMET ratio) → poorer PFS
- Arrow indicates same pt during the course of a HER1 inhibitor treatment Phospho cMET — cMET homodimer — cMET-PI3K complex — cMET-GAB1 complex P : phosphorylated residues
GO : Glucose Oxidase
HRP: Horse Radish Peroxidase

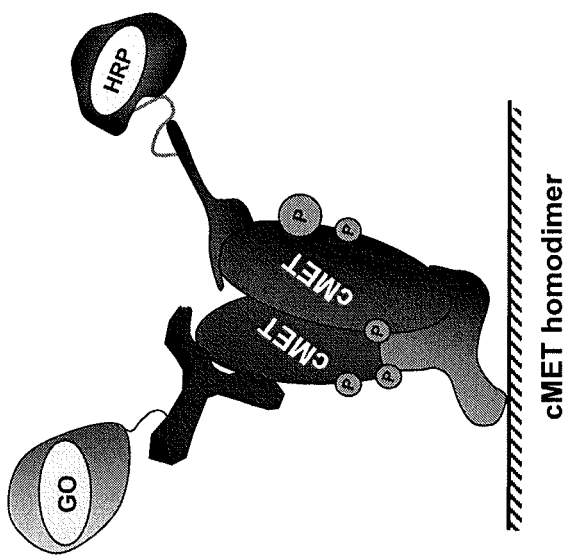
FIG. 12A
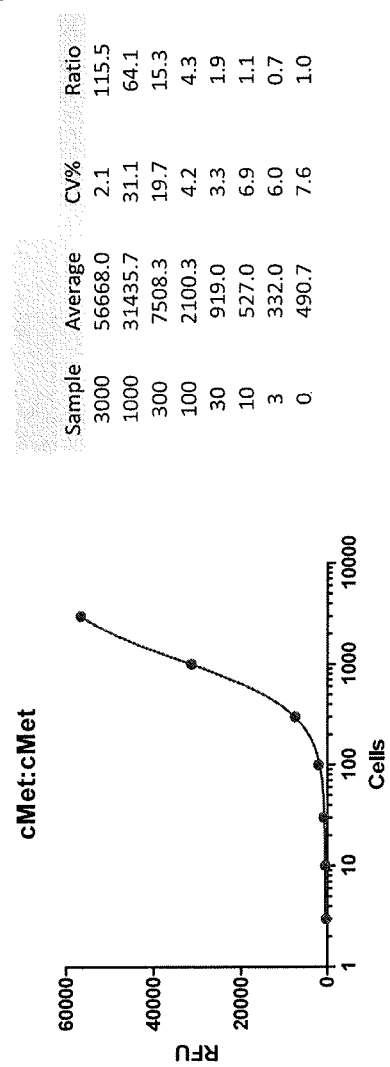
FIG. 12B
FIG. 12C
| Sample | Average | CV% | Ratio |
|---|---|---|---|
| 3000 | 56668.0 | 2.1 | 115.5 |
| 1000 | 31435.7 | 31.1 | 64.1 |
| 300 | 7508.3 | 19.7 | 15.3 |
| 100 | 2100.3 | 4.2 | 4.3 |
| 30 | 919.0 | 3.3 | 1.9 |
| 10 | 527.0 | 6.9 | 1.1 |
| 3 | 332.0 | 6.0 | 0.7 |
| 0 | 490.7 | 7.6 | 1.0 |

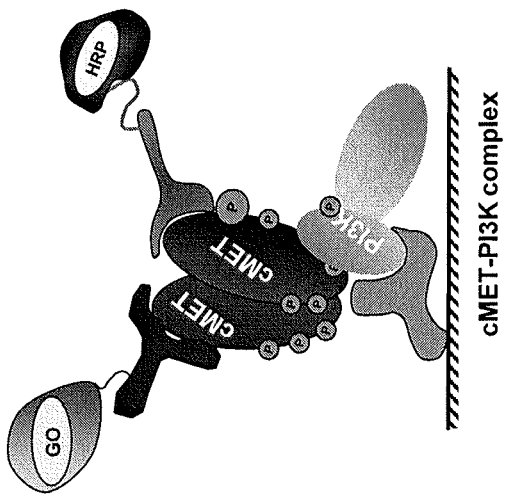
FIG. 13A
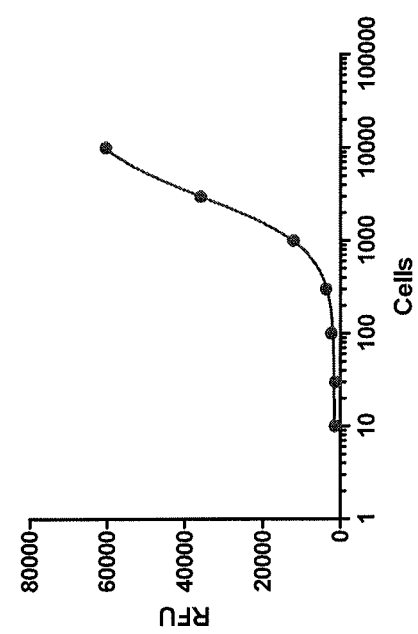
FIG. 13C
FIG. 13B

DRUG SELECTION FOR NON-SMALL CELL LUNG CANCER THERAPY

CROSS-REFERENCE TO RELATED APPLICATIONS

This application is a continuation of PCT/IB2014/058790, filed Feb. 4, 2014, which application claims priority to U.S. Provisional Patent Application No. 61/761,105, filed Feb. 5, 2013, the teachings of which are hereby incorporated by reference in its entirety for all purposes.

BACKGROUND OF THE INVENTION

Lung cancer is the leading cause of cancer-related mortality throughout the world. Approximately 80%-85% of all lung cancers are non-small cell lung cancer (NSCLC), which include squamous cell carcinoma, adenocarcinoma, and large-cell carcinoma. Current treatment options include surgical resection, platinum-based doublet chemotherapy with $3^{rd}$ generation chemotherapy including gemcitabine, docetaxel, paclitaxel, vinorelbine, irinotecan, or pemetrexed, and radiation therapy alone or in combination. Despite these therapies, the disease is rarely curable and prognosis is dismal, with an overall 5-year survival rate of only 15%.

The EGFR inhibitor therapy, have been extensively studied either alone or in combination with cytotoxic chemotherapy in NSCLC. However, the results overall show very small improvements in survival. The cumulative data from clinical trials with EGFR inhibitors suggest that different patients derive different degrees of clinical benefit from the treatment with EGFR inhibitors. These drugs have been shown to elicit partial responses in 10-20% of NSCLC patients (Fukuoko et al. *J. Clin. Oncol*, 21:2237-2246 (2003) and Kris et al. *JAMA*, 290:2149-2158 (2003)). Of those NSCLC patients harboring EGFR mutations and on EGFR-TKI therapy, 70-75% show a positive response rate (see, e.g. Yano et al., *Cancer Res.*, 68:9479-9487 (2008)). However, 25-30% of the patients are intrinsically resistant to EGFR-TKIs. Moreover, even those patients who are initial responders to treatment acquire resistance with time.

cMET inhibitor therapy is also under development for treating NSCLC because overexpression, activation and sometimes mutation of cMET have been detected in NSCLC cell lines and tumor tissues. For instance, 41-72% of lung tumors from patients with primary tumors exhibited increased cMet expression, and 8-13% of the tumors carried MET mutations. In addition, studies have shown that elevated expression of activated cMet significantly correlated to a shorter time to progression (TTP) in patients with NSCLC (Zucali et al., *Ann. Oncol.*, 19:1605-12 (2008)).

The implication of cMet signaling in tumor growth and progression has led to the development of a variety of anticancer drugs aimed at blocking cMet signaling. Holmes et al. (*J. Mol. Biol.*, 367:395-408, (2007)) describes that the N-terminus of HGF can bind, but not activate cMet signaling, suggesting that this may be an effective method of antagonizing the cMet pathway. Examples of current c-Met drugs under development include neutralizing antibodies such as MAG102 (Amgen) and MetMab (Roche), and tyrosine kinase inhibitors (TKIs) such as ARQ 197, XL 184, PF-02341066, GSK1363089/XL880, INC280, MP470, MGCD265, SGX523, PF04217903 and JNJ38877605. Preliminary clinical results of several of these drug agents have been encouraging.

The invention is based, in-part, on the surprising discovery of a method for identifying patients with NSCLC who will most likely benefit from EGFR inhibitor therapy and/or cMET inhibitor therapy. The methods of the invention can also be used to determine whether a patient receiving EGFR inhibitor therapy has acquired drug resistance.

BRIEF SUMMARY OF THE INVENTION

The present invention provides methods for therapy selection for a patient with NSCLC based on detecting, quantifying, and comparing the activity of particular signal transduction pathways, and components thereof, which can be represented as the patient's analyte index (e.g., EGFR/cMET index) and can be used to determine whether the patient is likely to respond to a particular therapy such as EGFR inhibitor therapy alone, cMET inhibitor therapy alone, or a combination thereof. Accordingly, knowledge of the EGFR/cMET index within a cancer cell prior to, during, and after treatment provides a physician with highly relevant information that can be used to select an appropriate course of treatment to adopt. Furthermore, the continued monitoring of signal transduction pathways, e.g. the EGFR pathway and the cMET pathway, that are active in cancer cells as treatment progresses can provide the physician with additional information on the efficacy of treatment, prompting the physician to either continue a particular course of treatment or to switch to another line of treatment, when, for example, cancer cells have become resistant to treatment through further aberrations that activate either the same or another signal transduction pathway.

Accordingly, the present invention provides a method for selecting a suitable anticancer drug for the treatment of non-small cell lung cancer (NSCLC) in a subject. The method comprises:
  (a) determining and/or quantifying the activation and/or expression level of EGFR in a cellular extract produced from an isolated cancer cell from the subject;
  (b) determining and/or quantifying the activation and/or expression level of c-Met in the cellular extract produced from an isolated cancer cell from the subject;
  (c) calculating a EGFR/c-MET index based upon the measurement of steps (a) and (b); and
  (d) selecting a suitable anticancer drug(s) for the treatment of NSCLC based upon the a EGFR/c-MET index.

In some embodiments, the expression levels of EGFR and cMet are used in calculating the EGFR/c-MET index. In other embodiments, the activation levels of EGFR and cMet are used in calculating the EGFR/c-MET index. In some instances, the expression levels and/or activation levels of EGFR and cMet are determined by CEER™. In other instances, the expression levels of EGFR and cMet are determined by mRNA. In some embodiments, the mRNA levels are measured using Northern blotting, Reverse Transcriptase Polymerase Chain Reaction (RT-PCR), or quantitative RT-PCR (qRT-PCR).

In some embodiments, the EGFR/c-MET index is between 1-20. In one embodiment, when the EGFR/c-MET index is between 2 and 20, the subject is administered an EGFR inhibitor. In another embodiment, when the EGFR/c-MET index is between 0 and 2, the subject is administered a cMET inhibitor or a combination of a cMET inhibitor and an EGFR inhibitor. In some instances, the level of pHER3 indicates EGFR inhibitor resistance. In another aspect, a low EGFR/c-MET index indicates progressive disease in the subject. In yet another aspect, a high EGFR/c-MET index indicates prolonged progression-free survival compared to a low EGFR/c-MET index.

In some embodiments, a EGFR mutation indicates prolonged progression-free survival compared to wild type EGFR. The EGFR mutation can be E709D, E709Q, E709K, E709A, E709A, G719S, G719C, G719A, G719R, S768I, T790M, L858R, L858M, L861Q or L861R.

In some embodiments, the method includes determining and/or quantifying the expression of HGF in lieu of (rather than) determining and/or quantifying the expression of cMET. In other embodiments, the method includes determining and/or quantifying the expression of cMET together with HGF in lieu of determining and/or quantifying the expression of cMET alone.

In another aspect, the present invention provides a method for monitoring a non-small cell lung cancer (NSCLC) subject receiving an anticancer drug. The method comprises:
 (a) detecting and/or quantifying the expression level and/or activation level of EGFR in a cellular extract produced from an isolated cancer cell from the subject;
 (b) detecting and/or quantifying the expression level and/or activation level of cMet in a cellular extract produced from an isolated cancer cell from the subject;
 (c) determining an EGFR/cMET index based on the activation and/or expression levels of EGFR and c-Met analytes in the cellular extracts at time point 1($t_1$);
 (d) repeating steps (a) and (b) to determine a EGFR/cMET index later in time based on the activation and/or expression levels of EGFR and c-Met analytes in the cellular extracts at time point 2 ($t_2$); and
 (e) comparing the EGFR/cMET index of the earlier time point ($t_1$) to the EGFR/cMET index at the later time point ($t_2$) to monitor the subject receiving the anticancer drug.

In some embodiments, an EGFR/cMET index at $t_2$ is greater than at $t_1$ indicates a longer progression-free survival (PFS) for the subject. In other embodiments, an EGFR/cMET index at $t_2$ is less than at $t_1$ indicates a shorter PFS for the subject. In yet other embodiments, an EGFR/cMET index at $t_2$ that is less than at $t_1$ indicates that the subject is resistant to EGFR inhibitor therapy. In further embodiments, a higher level of pHER3 at $t_2$ compared to $t_1$ indicates resistance to EGFR inhibitor therapy. In some instance, if the subject is determined to be resistant to EGFR therapy, a cMet inhibitor is included in the therapy for the subject.

In some embodiments, the expression levels of EGFR and cMet are used in calculating the EGFR/c-MET index. In other embodiments, the activation levels of EGFR and cMet are used in calculating the EGFR/c-MET index. In some instances, the expression levels and/or activation levels of EGFR and cMet are determined by CEER™. In other instances, the expression levels of EGFR and cMet are determined by mRNA. In some embodiments, the mRNA levels are measured using Northern blotting, Reverse Transcriptase Polymerase Chain Reaction (RT-PCR), or quantitative RT-PCR (qRT-PCR).

In some embodiments, the EGFR/c-MET index is between 0-20. In one embodiment, when the EGFR/c-MET index is between 2 and 20, the subject is administered an EGFR inhibitor. In another embodiment, when the EGFR/c-MET index is between 0 and 2, the subject is administered a cMET inhibitor or a combination of a cMET inhibitor and an EGFR inhibitor.

In some embodiments, the method includes determining and/or quantifying the expression of HGF in lieu of determining and/or quantifying the expression of cMET. In other embodiments, the method includes determining and/or quantifying the expression of cMET together with HGF in lieu of determining and/or quantifying the expression of cMET alone.

In some embodiments, the presence of an EGFR mutation indicates longer PFS compared to a subject with a wild type EGFR gene. In some instances, the EGFR mutation is selected from the group consisting of E709D, E709Q, E709K, E709A, E709A, G719S, G719C, G719A, G719R, S768I, T790M, L858R, L858M, L861Q and L861R.

In some embodiments, the EGFR inhibitor is selected from the group consisting of Cetaximab, Panitumumab, Matuzumab, Nimotuzumab, ErbB1 vaccine, Erlotinib, Gefitinib, EKB 569, CL-387-785 and a combination thereof.

In some embodiments, the c-MET inhibitor is selected from the group consisting of MAG102 and MetMab, ARQ197, XL184, PF-02341066, GSK1363089/XL880, MP470, MGCD265, SGX523, PF04217903, JNJ38877605, INCB28060, AMG-458, E7050, MK-2461, BMS-777607 and a combination thereof.

These and other aspects, objects and embodiments will become more apparent when read with the detailed description and figures that follow.

BRIEF DESCRIPTION OF THE DRAWINGS

FIGS. 1A-C represent analyte expression in a ratio to CK (creatine kinase; a reference control) expression in NSCLC patients with wildtype EGFR or activating EGFR mutations. FIG. 1A shows the total expression of HER1 relative to CK, cMET relative to CK and CK relative to CK (e.g., a ratio of 1) in patients with a EGFR mutation (left bar) and wildtype EGFR (right bar). FIG. 1B shows the total expression of HER2 relative to CK and IGFR1R relative to CK in patients with a EGFR mutation (left bar) and wildtype EGFR (right bar). FIG. 1C shows the total expression of HER3 relative to CK and PI3K relative to CK in patients with a EGFR mutation (left bar) and wildtype EGFR (right bar).

FIGS. 2A-C represent analyte expression in a ratio to PI3K (phosphoinositide-3-kinase; a reference control) expression in NSCLC patients with wildtype EGFR or activating EGFR mutations. FIG. 2A shows the total expression of HER1 relative to PI3K, cMET relative to PI3K and CK relative to PI3K in patients with a EGFR mutation (left bar) and wildtype EGFR (right bar). FIG. 2B shows the total expression of HER2 relative to PI3K and IGFR1R relative to PI3K in patients with a EGFR mutation (left bar) and wildtype EGFR (right bar). FIG. 2C shows the total expression of HER3 relative to PI3K and PI3K relative to PI3K (e.g., a ratio of 1) in patients with a EGFR mutation (left bar) and wildtype EGFR (right bar).

FIG. 3A shows a plot of EGFR/cMET index vs. progression-free survival in patients. Sample A was taken prior to EGFR inhibitor treatment. Sample B was taken 4 weeks into EGFR inhibitor treatment. Sample C was taken at the end of EGFR inhibitor treatment. FIG. 3B shows a plot of response to TKI therapy vs. EGFR/cMET index. The figure indicates that a low EGFR/cMET index is associated with progressive disease. PR: partial response. SD: stable disease. PD: progressive disease.

FIG. 4A shows EGFR/cMET index vs. time of progression-free survival in patients with wildtype EGFR. FIG. 4B shows EGFR/cMET index vs. time of progression-free survival in patients harboring EGFR mutation.

FIG. 5A shows Kaplan-Meier curves of all subjects. FIG. 5B shows Kaplan-Meier curves of all subjects stratified by the presence of EGFR mutation. The results indicated that EGFR mutant patients have better progression-free survival (e.g., longer than 8 months), which is in agreement with the art.

FIGS. 6A-C show Kaplan-Meier curves that stratify the patients into two groups: those above a specific EGFR/cMET index cut-off and those below that cut-off. FIG. 6A shows that an EGFR/cMET index of 6 which is equivalent to a level of p-EGFR 120 times higher (120×) than the level of p-cMET segregates the population into 6 patients above the cut-off and 23 patients below. FIG. 6B shows that at an EGFR/cMET index of 5 (or p-EGFR is 100× higher than p-cMET), there are 10 patients above the cut-off and 19 patients below and that the PFS of the two groups are not statistically different (p-value=0.054). FIG. 6C shows a similar curve with an EGFR/cMET index cut-off of 4 (or p-EGFR is 80× higher than p-cMET).

FIG. 7A shows that at an EGFR/cMET index cut-off of 3 (or p-EGFR is 60× higher than p-cMET), the patients below the cut-off have shorter progression-free survival compared to those above the cut-off. The difference of PFS (e.g., about 10 months) between the two groups is statistically significant (p-value=0.0001). FIG. 7B represents the data at an EGFR/cMET index cut-off of 2 (or p-EGFR is 40× higher than p-cMET). FIG. 7C represents the data at an EGFR/cMET index cut-off of 1 (or p-EGFR is 20× higher than p-cMET). These data demonstrates that patients with an EGFR/cMET index greater than 2 showed benefit from EGFR inhibitor treatment.

FIGS. 8A-C show Kaplan-Meier curves of patients with EGFR mutations and stratifying the patients into two groups: those above a specific EGFR/cMET index cut-off and those below. FIG. 8A represents data when the EGFR/cMET index cut-off is set at 6. FIG. 8B represents data when the EGFR/cMET index cut-off is set at 5. FIG. 8C represents data when the EGFR/cMET index cut-off is set at 4.

FIG. 9A represents data when the EGFR/cMET index cut-off is set at 3. FIG. 9B represents data when the EGFR/cMET index cut-off is set at 2. FIG. 9C represents data when the EGFR/cMET index cut-off is set at 1. Of EGFR mutant patients those with an EGFR/cMET index greater than 1 showed benefit from EGFR inhibitor treatment.

FIG. 11A depicts an embodiment for phospho-cMET. FIG. 11B shows an embodiment for cMET homodimer. FIG. 12C shows an embodiment for cMET:PI3K complexation. FIG. 11D depicts an embodiment for cMET:GAB1 complexation.

FIGS. 12A-C show an exemplary embodiment of the cMET homodimer assay. The complex was detectable in a sample of 30 cells. FIG. 12A shows an embodiment for cMET homodimer. FIGS. 12B and 12C show the performance of the assay with control cells that overexpress cMET protein.

FIGS. 13A-C show an exemplary assay of the present invention. FIG. 13A shows a cMET:PI3K complex assay. The complex was detectable in a sample of 300 cells. FIGS. 13B and 13C show the performance of the assay with control cells that express cMET:PI3K protein dimers.

DETAILED DESCRIPTION OF THE INVENTION

I. Introduction

Figure 7A:
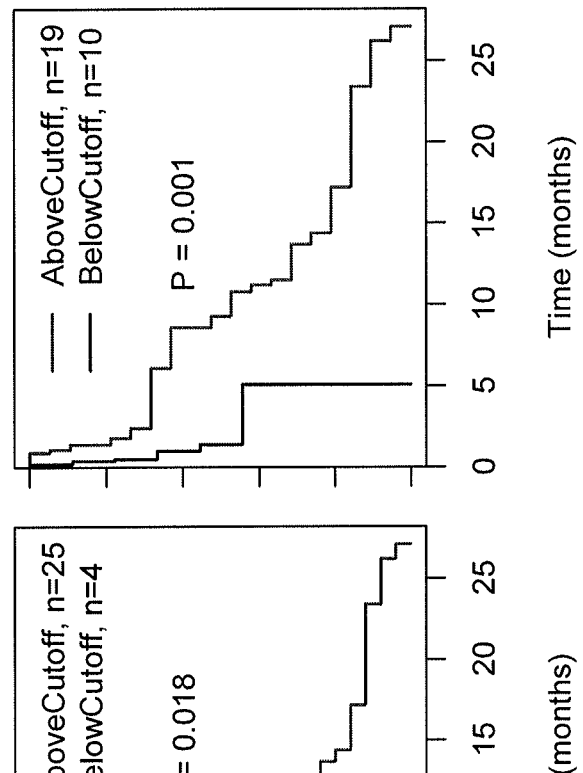
FIGS. 7A-C show more Kaplan-Meier curves that stratify the patients into two groups: those above a specific EGFR/cMET index cut-off and those below that cut-off.

A current problem with selecting an effective therapeutic strategy for non-small cell lung cancer (NSCLC) patients is due to the high incidence of intrinsic and acquired resistance to anticancer drug treatments (e.g., tyrosine kinase inhibitors). For example, a subset of patients with NSCLC are intrinsically resistant to EGFR TKIs. And even those initially responsive to the therapy tend to become resistant over time. The present invention overcomes or mitigates this problem as well as others by providing methods for the selection of appropriate therapy (single drugs or combinations of drugs) based on an predictive index of a plurality of dysregulated signal transduction molecules in tumor tissue of a solid tumor as determined by a specific, multiplex, high-throughput assay, such as a Collaborative Enzyme Enhanced Reactive Immunoassay (CEER). As such, the detection of the activation state of multiple signal transducers, including cMET and HER family members, in rare cells in tumors facilitates cancer prognosis and diagnosis as well as the design of personalized, targeted therapies.

II. Definitions

As used herein, the following terms have the meanings ascribed to them unless specified otherwise.

The term "a" or "an" is generally employed in its sense including "one," "single," "more than one," or "plurality" unless the content clearly dictates otherwise. For instance, "a cell" includes one cell, more than one cell, a group of cells, or a plurality of cells.

The term "cancer" is intended to include any member of a class of diseases characterized by the uncontrolled growth of aberrant cells. The term includes all known cancers and neoplastic conditions, whether characterized as malignant, benign, soft tissue, or solid, and cancers of all stages and grades including pre- and post-metastatic cancers. Examples of different types of cancer include, but are not limited to, digestive and gastrointestinal cancers such as gastric cancer (e.g., stomach cancer), colorectal cancer, gastrointestinal stromal tumors (GIST), gastrointestinal carcinoid tumors, colon cancer, rectal cancer, anal cancer, bile duct cancer, small intestine cancer, and esophageal cancer; breast cancer; lung cancer (e.g., non-small cell lung cancer (NSCLC)); gallbladder cancer; liver cancer; pancreatic cancer; appendix cancer; prostate cancer; ovarian cancer; renal cancer (e.g., renal cell carcinoma); cancer of the central nervous system; skin cancer; lymphomas; gliomas; choriocarcinomas; head and neck cancers; osteogenic sarcomas; and blood cancers. As used herein, a "tumor" comprises one or more cancerous cells.

The term "non-small cell lung cancer" or "NSCLC" includes a disease in which malignant cancer cells form in the tissues of the lung. Examples of non-small cell lung cancers include, but are not limited to, squamous cell carcinoma, large cell carcinoma, and adenocarcinoma.

The term "analyte" includes any molecule of interest, typically a macromolecule such as a polypeptide, whose presence, amount (expression level), activation state, and/or identity is determined. In certain instances, the analyte is a signal transduction molecule such as, e.g., a component of an EGFR (HER1) or cMet signaling pathway.

The term "signal transduction molecule" or "signal transducer" includes proteins and other molecules that carry out the process by which a cell converts an extracellular signal or stimulus into a response, typically involving ordered sequences of biochemical reactions inside the cell. Examples of signal transduction molecules include, but are not limited to, receptor tyrosine kinases such as EGFR (e.g., EGFR/HER1/ErbB1, HER2/Neu/ErbB2, HER3/ErbB3, HER4/ErbB4), VEGFR1/FLT1, VEGFR2/FLK1/KDR, VEGFR3/FLT4, FLT3/FLK2, PDGFR (e.g., PDGFRA, PDGFRB), c-KIT/SCFR, INSR (insulin receptor), IGF-IR, IGF-IIR, IRR (insulin receptor-related receptor), CSF-1R, FGFR 1-4, HGFR 1-2, CCK4, TRK A-C, c-MET, RON, EPHA 1-8, EPHB 1-6, AXL, MER, TYRO3, TIE 1-2, TEK, RYK, DDR 1-2, RET, c-ROS, V-cadherin, LTK (leukocyte tyrosine kinase), ALK (anaplastic lymphoma kinase), ROR 1-2, MUSK, AATYK 1-3, and RTK 106; truncated forms of receptor tyrosine kinases such as truncated HER2 receptors with missing amino-terminal extracellular domains (e.g., p95ErbB2 (p95m), p110, p95c, p95n, etc.), truncated cMET receptors with missing amino-terminal extracellular domains, and truncated HER3 receptors with missing amino-terminal extracellular domains; receptor tyrosine kinase dimers (e.g., p95HER2/HER3; p95HER2/HER2; truncated HER3 receptor with HER1, HER2, HER3, or HER4; HER2/HER2; HER3/HER3; HER2/HER3; HER1/HER2; HER1/HER3; HER2/HER4; HER3/HER4; etc.); non-receptor tyrosine kinases such as BCR-ABL, Src, Frk, Btk, Csk, Abi, Zap70, Fes/Fps, Fak, Jak, Ack, and LIMK; tyrosine kinase signaling cascade components such as AKT (e.g., AKT1, AKT2, AKT3), MEK (MAP2K1), ERK2 (MAPK1), ERK1 (MAPK3), PI3K (e.g., PIK3CA (p110), PIK3R1 (p85)), PDK1, PDK2, phosphatase and tensin homolog (PTEN), SGK3, 4E-BP1, P70S6K (e.g., p70 S6 kinase splice variant alpha I), protein tyrosine phosphatases (e.g., PTP1B, PTPN13, BDP1, etc.), RAF, PLA2, MEKK, JNKK, JNK, p38, Shc (p66), Ras (e.g., K-Ras, N-Ras, H-Ras), Rho, Racl, Cdc42, PLC, PKC, p53, cyclin D1, STAT1, STAT3, phosphatidylinositol 4,5-bisphosphate (PIP2), phosphatidylinositol 3,4,5-trisphosphate (PIP3), mTOR, BAD, p21, p27, ROCK, IP3, TSP-1, NOS, GSK-3β, RSK 1-3, JNK, c-Jun, Rb, CREB, Ki67, and paxillin; nuclear hormone receptors such as estrogen receptor (ER), progesterone receptor (PR), androgen receptor, glucocorticoid receptor, mineralocorticoid receptor, vitamin A receptor, vitamin D receptor, retinoid receptor, thyroid hormone receptor, and orphan receptors; nuclear receptor coactivators and repressors such as amplified in breast cancer-1 (AIB1) and nuclear receptor corepressor 1 (NCOR), respectively; and combinations thereof.

The terms "EGFR", "epidermal growth factor receptor" and "ERBB1" and "HER1" are used interchangeably herein and refer to native sequence EGFR as disclosed, for example, in Carpenter et al. Ann. Rev. Biochem. 56:881-914 (1987), including variants thereof (e.g. a deletion mutant EGFR as in Humphrey et al. PNAS (USA) 87:4207-4211 (1990)). erbB1 refers to the gene encoding the EGFR protein product. Examples of antibodies which bind to EGFR include MAb 579 (ATCC CRL RB 8506), MAb 455 (ATCC CRL HB8507), MAb 225 (ATCC CRL 8508), MAb 528 (ATCC CRL 8509) (see, U.S. Pat. No. 4,943,533, Mendelsohn et al.) and variants thereof, such as chimerized 225 (C225) and reshaped human 225 (H225) (see, WO 96/40210, Imclone Systems Inc.).

The terms "HER3" and "ERbB3" refer to the receptor polypeptide as disclosed, for example, in U.S. Pat. Nos. 5,183,884 and 5,480,968 as well as Kraus et al. PNAS (USA) 86:9193-9197 (1989), including variants thereof. Examples of antibodies which bind HER3 are described in U.S. Pat. No. 5,968,511, e.g. the 8B8 antibody (ATCC HB 12070).

The term "component of a HER3 signaling pathway" includes any one or more of an upstream ligand of HER3, binding partner of HER3, and/or downstream effector molecule that is modulated through HER3. Examples of HER3 signaling pathway components include, but are not limited to, heregulin, HER1/ErbB1, HER2/ErbB2, HER3/ErbB3, HER4/ErbB4, AKT (e.g., AKT1, AKT2, AKT3), MEK (MAP2K1), ERK2 (MAPK1), ERK1 (MAPK3), PI3K (e.g., PIK3CA (p110), PIK3R1 (p85)), PDK1, PDK2, PTEN, SGK3, 4E-BP1, P70S6K (e.g., splice variant alpha I), protein tyrosine phosphatases (e.g., PTP1B, PTPN13, BDP1, etc.), HER3 dimers (e.g., p95HER2/HER3, HER2/HER3, HER3/HER3, HER3/HER4, etc.), GSK-3β, PIP2, PIP3, p27, and combinations thereof.

The term "component of a c-Met signaling pathway" includes any one or more of an upstream ligand of c-Met, binding partner of c-Met, and/or downstream effector molecule that is modulated through c-Met. Examples of c-Met signaling pathway components include, but are not limited to, hepatocyte growth factor/scatter factor (HGF/SF), Plexin B1, CD44v6, AKT (e.g., AKT1, AKT2, AKT3), MEK (MAP2K1), ERK2 (MAPK1), ERK1 (MAPK3), STAT (e.g., STAT1, STAT3), PI3K (e.g., PIK3CA (p110), PIK3R1 (p85)), GRB2, Shc (p66), Ras (e.g., K-Ras, N-Ras, H-Ras), GAB1, SHP2, SRC, GRB2, CRKL, PLCγ, PKC (e.g., PKCα, PKCβ, PKCδ), paxillin, FAK, adducin, RB, RB1, PYK2, and combinations thereof.

The term "aberrant c-Met signaling" refers to deregulation of one or more of the c-Met signaling pathway components due to causes such as, but not limited to, activation of the c-Met receptor via genomic alterations, changes in protein expression levels, changes in activated protein levels, and increased ligand stimulation. Examples of c-Met signaling pathway components include, but are not limited to, those described herein.

The term "truncated c-Met protein" includes a truncated form of the c-Met receptor that includes, but is not limited to, a protein containing the cytoplasmic and juxtamembrane domains of c-Met (see, e.g., Amicone et al., *Gene*, 162: 323-328 (1995) and Amicone et al., *Oncogene*, 21: 1335-1345); a protein containing the extracellular domain of c-Met; a protein comprising the alpha-chain and the 85-kDa C-terminal truncated beta-chain of c-Met (see, e.g., Prat et al., *Mol. Cell. Biol.* 11:5954-5962 (1991)); and a protein comprising the alpha-chain and the 75-kDa C-terminal truncated beta chain-of c-Met (see, e.g., Prat et al., *Mol. Cell. Biol.*, 11:5954-5962 (1991)). In certain instances, the truncated receptor is typically a fragment of the full-length receptor and shares an intracellular domain (ICD) binding region with the full-length receptor. In certain embodiments, the full-length receptor comprises an extracellular domain (ECD) binding region, a transmembrane domain, and an intracellular domain (ICD) binding region. Without being bound to any particular theory, the truncated receptor may arise through the proteolytic processing of the ECD of the full-length receptor or by alternative initiation of translation from methionine residues that are located before, within, or after the transmembrane domain, e.g., to create a truncated c-Met receptor with a shortened ECD or a truncated c-Met receptor comprising a membrane-associated or cytosolic ICD fragment.

The term "truncated HER3 protein" includes a truncated form of the HER3 receptor that includes, but is not limited to, a protein containing the cytoplasmic and juxtamembrane domains of HER3; a truncated extracellular fragment of HER3 of 140 amino acids followed by 43 unique residues (see, e.g., Srinivasan et al., Cell Signal, 13:321-30 (2001)); and a 45-kDa glycosylated HER3 protein (see, e.g., Lin et al., Oncogene, 0.27:5195-5203 (2008)). In certain instances, the truncated receptor is typically a fragment of the full-length receptor and shares an intracellular domain (ICD) binding region with the full-length receptor. In certain embodiments, the full-length receptor comprises an extracellular domain (ECD) binding region, a transmembrane domain, and an intracellular domain (ICD) binding region. Without being bound to any particular theory, the truncated receptor may arise through the proteolytic processing of the ECD of the full-length receptor or by alternative initiation of translation from methionine residues that are located before, within, or after the transmembrane domain, e.g., to create a truncated HER3 receptor with a shortened ECD or a truncated HER3 receptor comprising a membrane-associated or cytosolic ICD fragment.

The term "activation state" refers to whether a particular signal transduction molecule such as a HER3 or c-Met signaling pathway component is activated. Similarly, the term "activation level" refers to what extent a particular signal transduction molecule such as a HER3 or c-Met signaling pathway component is activated. The activation state typically corresponds to the phosphorylation, ubiquitination, and/or complexation status of one or more signal transduction molecules. Non-limiting examples of activation states (listed in parentheses) include: HER1/EGFR (EGFRvIII, phosphorylated (p-) EGFR, EGFR:Shc, ubiquitinated (u-) EGFR, p-EGFRvIII); ErbB2 (p-ErbB2, p95HER2 (truncated ErbB2), p-p95HER2, ErbB2:Shc, ErbB2:PI3K, ErbB2:EGFR, ErbB2:ErbB3, ErbB2:ErbB4); ErbB3 (p-ErbB3, truncated ErbB3, ErbB3:PI3K, p-ErbB3:PI3K, ErbB3:Shc); ErbB4 (p-ErbB4, ErbB4:Shc); c-MET (p-c-MET, truncated c-MET, c-Met:HGF complex); AKT1 (p-AKT1); AKT2 (p-AKT2); AKT3 (p-AKT3); PTEN (p-PTEN); P70S6K (p-P70S6K); MEK (p-MEK); ERK1 (p-ERK1); ERK2 (p-ERK2); PDK1 (p-PDK1); PDK2 (p-PDK2); SGK3 (p-SGK3); 4E-BP1 (p-4E-BP1); PIK3R1 (p-PIK3R1); c-KIT (p-c-KIT); ER (p-ER); IGF-1R (p-IGF-1R, IGF-1R:IRS, IRS:PI3K, p-IRS, IGF-1R:PI3K); INSR (p-INSR); FLT3 (p-FLT3); HGFR1 (p-HGFR1); HGFR2 (p-HGFR2); RET (p-RET); PDGFRA (p-PDGFRA); PDGFRB (p-PDGFRB); VEGFR1 (p-VEGFR1, VEGFR1:PLCγ, VEGFR1:Src); VEGFR2 (p-VEGFR2, VEGFR2:PLCγ, VEGFR2:Sre, VEGFR2:heparin sulphate, VEGFR2:VE-cadherin); VEGFR3 (p-VEGFR3); FGFR1 (p-FGFR1); FGFR2 (p-FGFR2); FGFR3 (p-FGFR3); FGFR4 (p-FGFR4); TIE1 (p-TIE1); TIE2 (p-TIE2); EPHA (p-EPHA); EPHB (p-EPHB); GSK-3β (p-GSK-3β); NFKB (p-NFKB), IKB (p-IKB, p-P65:IKB); BAD (p-BAD, BAD:14-3-3); mTOR (p-mTOR); Rsk-1 (p-Rsk-1); Jnk (p-Jnk); P38 (p-P38); STAT1 (p-STAT1); STAT3 (p-STAT3); FAK (p-FAK); RB (p-RB); Ki67; p53 (p-p53); CREB (p-CREB); c-Jun (p-c-Jun); c-Src (p-c-Src); paxillin (p-paxillin); GRB2 (p-GRB2), She (p-Shc), Ras (p-Ras), GAB1 (p-GAB1), SHP2 (p-SHP2), GRB2 (p-GRB2), CRKL (p-CRKL), PLCγ (p-PLCγ), PKC (e.g., p-PKCα, p-PKCβ, p-PKCδ), adducin (p-adducin), RB1 (p-RB1), and PYK2 (p-PYK2).

The term "KRAS mutation" includes any one or more mutations in the KRAS (which can also be referred to as KRAS2 or RASK2) gene. Examples of KRAS mutations include, but are not limited to, G12C, G12D, G13D, G12R, and G12V.

The term "EGFR mutation" includes any one or more mutations in the EGFR (which can also be referred to as ErbB1 or HER1) gene. Examples of EGFR mutations include, but are not limited to, mutations in exon 18 such as E709D/Q/KA/H and G719S/C/A/R, deletions in exon 19, mutations in exon 20, such as S768 and T790M, and mutations in exon 21 such as L858R/M and L861Q/R.

The term "pathway-directed therapy" includes the use of therapeutic agents which can alter the expression level and/or activated level of proteins.

The term "cMet inhibitor" includes a therapeutic agent that interferes with the function of cMet pathway components. Examples of cMet inhibitors include, but are not limited to, neutralizing antibodies such as MAG102 (Amgen) and MetMab (Roche), and tyrosine kinase inhibitors (TKIs) such as ARQ197, XL184, PF-02341066, GSK1363089/XL880, MP470, MGCD265, SGX523, PF04217903 JNJ38877605, INCB28060, AMG-458, E7050, MK-2461, and BMS-777607.

The term "EGFR inhibitor" includes a therapeutic agent that interferes with the function of EGFR pathway components. Non-limiting examples include Cetaximab, Panitumumab, Matuzumab, Nimotuzumab, ErbB1 vaccine, Erlotinib, Gefitinib, EKB 569, and CL-387-785.

The term "serial changes" includes the ability of an assay to detect changes in the expression level and/or activation level of a protein in a sample taken from a subject at different points in time. For example, the expression level and/or activation level of cMet protein can be monitored in a patient during the course of therapy, including a time prior to starting therapy.

The term "negative response" includes a worsening of a disease condition in a patient receiving therapy, such that the patient experiences increased or additional signs or symptoms of the disease.

The term "positive response" includes an improvement in a patient with a disease condition, such that the therapy alleviates signs or symptoms of the disease.

The term "disease remission" includes a classification of a cancer wherein there is a disappearance in the signs and symptoms of the disease.

The term "disease progression" includes a classification of a cancer that continues to grow or spread, which can lead to additional signs or symptoms of cancer. For example, the recurrence of tumors in lung tissue in patients with NSCLC is described herein as disease progression.

The term "response rate" or "RR" includes the percentage of patients with positive responses, such as tumor shrinkage or disappearance, to a defined therapy for the treatment of a disease.

The term "complete response" or "complete remission" or "CR" includes the clinical endpoint described by the disappearance of all signs of cancer in response to treatment after a period of time. For example, if at the end of the time or treatment course, there is no residual disease that can be identified by measurements of symptom control and quality of life as performed by examination, X-ray and scan, or analysis of biomarkers of the disease, the patient is described herein to exhibit complete response to therapy. In certain instances, complete response is the disappearance of all tumor lesions (see, National Cancer Institute's Response Evaluation Criteria in Solid Tumors (RECIST), updated in January 2009).

The term "partial response" or "PR" includes a clinical endpoint described as the disappearance of some, but not all signs of cancer in response to treatment after a period of time. For example, if at the end of the time or treatment course, there is some detectable residual disease that can be identified by measurements of symptom control and quality of life as performed by examination, X-ray and scan, or analysis of biomarkers of the disease, the patient is described herein to exhibit partial response to therapy. In certain instances, partial response is a 30% decrease in the sum of the longest diameter of the tumor lesions (see, National Cancer Institute's Response Evaluation Criteria in Solid Tumors (RECIST), updated in January 2009).

The term "stable disease" or "SD" includes a clinical endpoint in cancer characterized by the appearance of no new tumors and no substantial change in the size of existing, known tumors. According to RECIST, stable disease is defined as small changes that do not meet the criteria of complete response, partial response, and progressive disease (which is defined as a 20% increase in the sum of the longest diameter of the tumor lesions).

The term "time to progression" or "TTP" includes the measure of time after a disease is diagnosed or treated until the disease starts to worsen (e.g., appearance of new tumors, increase in tumor size; change in the quality of life, or change in symptom control).

The term "progression free survival" or "PFS" includes the length of time during and after a treatment of a disease in which a patient is living with the disease without additional symptoms of the disease.

The term "overall survival" or "OS" includes the clinical endpoint describing patients who are alive for a defined period of time after being diagnosed with or treated for a disease, such as cancer.

As used herein, the term "dilution series" is intended to include a series of descending concentrations of a particular sample (e.g., cell lysate) or reagent (e.g., antibody). A dilution series is typically produced by a process of mixing a measured amount of a starting concentration of a sample or reagent with a diluent (e.g., dilution buffer) to create a lower concentration of the sample or reagent, and repeating the process enough times to obtain the desired number of serial dilutions. The sample or reagent can be serially diluted at least 2, 3, 4, 5, 6, 7, 8, 9, 10, 15, 20, 25, 30, 35, 40, 45, 50, 100, 500, or 1000-fold to produce a dilution series comprising at least 2, 3, 4, 5, 6, 7, 8, 9, 10, 11, 12, 13, 14, 15, 16, 17, 18, 19, 20, 25, 30, 35, 40, 45, or 50 descending concentrations of the sample or reagent. For example, a dilution series comprising a 2-fold serial dilution of a capture antibody reagent at a 1 mg/ml starting concentration can be produced by mixing an amount of the starting concentration of capture antibody with an equal amount of a dilution buffer to create a 0.5 mg/ml concentration of the capture antibody, and repeating the process to obtain capture antibody concentrations of 0.25 mg/ml, 0.125 mg/ml, 0.0625 mg/ml, 0.0325 mg/ml, etc.

The term "superior dynamic range" as used herein refers to the ability of an assay to detect a specific analyte in as few as one cell or in as many as thousands of cells. For example, the immunoassays described herein possess superior dynamic range because they advantageously detect a particular signal transduction molecule of interest in about 1-10,000 cells (e.g., about 1, 5, 10, 25, 50, 75, 100, 250, 500, 750, 1000, 2500, 5000, 7500, or 10,000 cells) using a dilution series of capture antibody concentrations.

As used herein, the term "circulating cells" comprises extratumoral cells that have either metastasized or micrometastasized from a solid tumor. Examples of circulating cells include, but are not limited to, circulating tumor cells, cancer stem cells, and/or cells that are migrating to the tumor (e.g., circulating endothelial progenitor cells, circulating endothelial cells, circulating pro-angiogenic myeloid cells, circulating dendritic cells, etc.). Patient samples containing circulating cells can be obtained from any accessible biological fluid (e.g., whole blood, serum, plasma, sputum, bronchial lavage fluid, urine, nipple aspirate, lymph, saliva, fine needle aspirate, etc.). In certain instances, the whole blood sample is separated into a plasma or serum fraction and a cellular fraction (i.e., cell pellet). The cellular fraction typically contains red blood cells, white blood cells, and/or circulating cells of a solid tumor such as circulating tumor cells (CTCs), circulating endothelial cells (CECs), circulating endothelial progenitor cells (CEPCs), cancer stem cells (CSCs), disseminated tumor cells of the lymph node, and combinations thereof. The plasma or serum fraction usually contains, inter alia, nucleic acids (e.g., DNA, RNA) and proteins that are released by circulating cells of a solid tumor.

Circulating cells are typically isolated from a patient sample using one or more separation methods including, for example, immunomagnetic separation (see, e.g., Racila et al., *Proc. Natl. Acad. Sci. USA*, 95:4589-4594 (1998); Bilkenroth et al., *Int. J. Cancer*, 92:577-582 (2001)), the Cell-Tracks® System by Immunicon (Huntingdon Valley, Pa.), microfluidic separation (see, e.g., Mohamed et al., *IEEE Trans. Nanobiosci.*, 3:251-256 (2004); Lin et al., Abstract No. 5147, 97th AACR Annual Meeting, Washington, D.C. (2006)), FACS (see, e.g., Mancuso et al., *Blood*, 97:3658-3661 (2001)), density gradient centrifugation (see, e.g., Baker et al., *Clin. Cancer Res.*, 13:4865-4871 (2003)), and depletion methods (see, e.g., Meye et al., *Int. J. Oncol.*, 21:521-530 (2002)).

The term "sample" as used herein includes any biological specimen obtained from a patient. Samples include, without limitation, whole blood, plasma, serum, red blood cells, white blood cells (e.g., peripheral blood mononuclear cells), ductal lavage fluid, nipple aspirate, lymph (e.g., disseminated tumor cells of the lymph node), bone marrow aspirate, saliva, urine, stool (i.e., feces), sputum, bronchial lavage fluid, tears, fine needle aspirate (e.g., harvested by random periareolar fine needle aspiration), any other bodily fluid, a tissue sample (e.g., tumor tissue) such as a biopsy of a tumor (e.g., needle biopsy) or a lymph node (e.g., sentinel lymph node biopsy), a tissue sample (e.g., tumor tissue) such as a surgical resection of a tumor, and cellular extracts thereof. In some embodiments, the sample is whole blood or a fractional component thereof such as plasma, serum, or a cell pellet. In preferred embodiments, the sample is obtained by isolating circulating cells of a solid tumor from whole blood or a cellular fraction thereof using any technique known in the art. In other embodiments, the sample is a formalin fixed paraffin embedded (FFPE) tumor tissue sample, e.g., from a solid tumor of the stomach or other portion of the gastrointestinal tract.

A "biopsy" refers to the process of removing a tissue sample for diagnostic or prognostic evaluation, and to the tissue specimen itself. Any biopsy technique known in the art can be applied to the methods and compositions of the present invention. The biopsy technique applied will generally depend on the tissue type to be evaluated and the size and type of the tumor (i.e., solid or suspended (i.e., blood or ascites)), among other factors. Representative biopsy techniques include excisional biopsy, incisional biopsy, needle biopsy (e.g., core needle biopsy, fine-needle aspiration biopsy, etc.), surgical biopsy, and bone marrow biopsy. Biopsy techniques are discussed, for example, in *Harrison's Principles of Internal Medicine*, Kasper, et al., eds., 16th ed., 2005, Chapter 70, and throughout Part V. One skilled in the art will appreciate that biopsy techniques can be performed to identify cancerous and/or precancerous cells in a given tissue sample.

The term "subject" or "patient" or "individual" typically includes humans, but can also include other animals such as, e.g., other primates, rodents, canines, felines, equines, ovines, porcines, and the like.

An "array" or "microarray" comprises a distinct set and/or dilution series of capture antibodies immobilized or restrained on a solid support such as, for example, glass (e.g., a glass slide), plastic, chips, pins, filters, beads (e.g., magnetic beads, polystyrene beads, etc.), paper, membrane (e.g., nylon, nitrocellulose, polyvinylidene fluoride (PVDF), etc.), fiber bundles, or any other suitable substrate. The capture antibodies are generally immobilized or restrained on the solid support via covalent or noncovalent interactions (e.g., ionic bonds, hydrophobic interactions, hydrogen bonds, Van der Waals forces, dipole-dipole bonds). In certain instances, the capture antibodies comprise capture tags which interact with capture agents bound to the solid support. The arrays used in the assays described herein typically comprise a plurality of different capture antibodies and/or capture antibody concentrations that are coupled to the surface of a solid support in different known/addressable locations.

The term "capture antibody" is intended to include an immobilized antibody which is specific for (i.e., binds, is bound by, or forms a complex with) one or more analytes of interest in a sample such as a cellular extract. In particular embodiments, the capture antibody is restrained on a solid support in an array. Suitable capture antibodies for immobilizing any of a variety of signal transduction molecules on a solid support are available from Upstate (Temecula, Calif.), Biosource (Camarillo, Calif.), Cell Signaling Technologies (Danvers, Mass.), R&D Systems (Minneapolis, Minn.), Lab Vision (Fremont, Calif.), Santa Cruz Biotechnology (Santa Cruz, Calif.), Sigma (St. Louis, Mo.), and BD Biosciences (San Jose, Calif.).

The term "detection antibody" as used herein includes an antibody comprising a detectable label which is specific for (i.e., binds, is bound by, or forms a complex with) one or more analytes of interest in a sample. The term also encompasses an antibody which is specific for one or more analytes of interest, wherein the antibody can be bound by another species that comprises a detectable label. Examples of detectable labels include, but are not limited to, biotin/streptavidin labels, nucleic acid (e.g., oligonucleotide) labels, chemically reactive labels, fluorescent labels, enzyme labels, radioactive labels, and combinations thereof. Suitable detection antibodies for detecting the activation state and/or total amount of any of a variety of signal transduction molecules are available from Upstate (Temecula, Calif.), Biosource (Camarillo, Calif.), Cell Signaling Technologies (Danvers, Mass.), R&D Systems (Minneapolis, Minn.), Lab Vision (Fremont, Calif.), Santa Cruz Biotechnology (Santa Cruz, Calif.), Sigma (St. Louis, Mo.), and BD Biosciences (San Jose, Calif.). As a non-limiting example, phosphospecific antibodies against various phosphorylated forms of signal transduction molecules such as EGFR, HER2, HER3, cMET, IGF1R, PI3K, SHC, and others are available from Santa Cruz Biotechnology.

The term "activation state-dependent antibody" includes a detection antibody which is specific for (i.e., binds, is bound by, or forms a complex with) a particular activation state of one or more analytes of interest in a sample. In preferred embodiments, the activation state-dependent antibody detects the phosphorylation, ubiquitination, and/or complexation state of one or more analytes such as one or more signal transduction molecules. In some embodiments, the phosphorylation of members of the EGFR family of receptor tyrosine kinases and/or the formation of heterodimeric complexes between EGFR family members is detected using activation state-dependent antibodies. In particular embodiments, activation state-dependent antibodies are useful for detecting one or more sites of phosphorylation in one or more of the following signal transduction molecules (phosphorylation sites correspond to the position of the amino acid in the human protein sequence): EGFR/HER1/ErbB1 (e.g., tyrosine (Y) 1068); ErbB2/HER2 (e.g., Y1248); ErbB3/HER3 (e.g., Y1289); ErbB4/HER4 (e.g., Y1284); c-Met (e.g., Y1003, Y1230, Y1234, Y1235, and/or Y1349); SGK3 (e.g., threonine (T) 256 and/or serine (S) 422); 4E-BP1 (e.g., T70); ERK1 (e.g., T185, Y187, T202, and/or Y204); ERK2 (e.g., T185, Y187, T202, and/or Y204); MEK (e.g., S217 and/or S221); PIK3R1 (e.g., Y688); PDK1 (e.g., S241); P70S6K (e.g., T229, T389, and/or S421); PTEN (e.g., S380); AKT1 (e.g., S473 and/or T308); AKT2 (e.g., S474 and/or T309); AKT3 (e.g., S472 and/or T305); GSK-3β (e.g., S9); NFKB (e.g., S536); IKB (e.g., S32); BAD (e.g., S112 and/or S136); mTOR (e.g., S2448); Rsk-1 (e.g., T357 and/or S363); Jnk (e.g., T183 and/or Y185); P38 (e.g., T180 and/or Y182); STAT3 (e.g., Y705 and/or S727); FAK (e.g., Y397, Y576, S722, Y861, and/or S910); RB (e.g., S249, T252, S612, and/or S780); RB1 (e.g., S780); adducin (e.g., S662 and/or S724); PYK2 (e.g., Y402 and/or Y881); PKCα (e.g., S657); PKCα/β (e.g., T368 and/or T641); PKCδ (e.g., T505); p53 (e.g., S392 and/or S20); CREB (e.g., S133); c-Jun (e.g., S63); c-Src (e.g., Y416); and paxillin (e.g., Y31 and/or Y118).

The term "activation state-independent antibody" includes a detection antibody which is specific for (i.e., binds, is bound by, or forms a complex with) one or more analytes of interest in a sample irrespective of their activation state. For example, the activation state-independent antibody can detect both phosphorylated and unphosphorylated forms of one or more analytes such as one or more signal transduction molecules.

Non-limiting examples of activation state-independent c-Met antibodies include those available under the following catalog numbers: AF276, MAB3581, MAB3582, MAB3583, and MAB5694 (R&D Systems); ab51067, ab39075, ab47431, ab14571, ab10728, ab59884, ab47431, ab49210, ab71758, ab74217, ab47465, ab27492 (Abcam); SC161HRP (Santa Cruz); PA1-14257, PA1-37483, and PA1-37484 (Thermo Scientific); 05-1049, MAB3729 (Millipore); sc-162, sc-34405, sc-161, sc-10, sc-8307, sc-46394, sc-46395, sc-81478 (Santa Cruz Biotechnology); 8198, 3127, 3148, and 4560 (Cell Signaling Technology); and 700261, 370100, 718000 (Life Technologies).

Non-limiting examples of activation state-dependent cMET antibodies include those available under the following catalog numbers: AF2480, AF3950, AF4059 (R&D Systems); PA1-14254, PA1-14256 (Thermo Scientific); sc-16315, sc-34086, sc34085, sc-34087, sc-101736, sc-101737 (Santa Cruz Biotechnology); ab61024, ab5662, ab73992, and ab5656 (Abcam); 3135, 3077, 3129, 3126, 3133, 3121 (Cell Signaling Technology); and 44892G, 44896G, 700139, 44887G, 44888G, 44882G (Life Technologies).

Non-limiting examples of capture antibodies that recognize cMET include those available under the following catalog numbers: AF276, MAB3581, MAB3582, MAB3583, and MAB5694 (R&D Systems); ab51067, ab39075, ab47431, ab14571, ab10728, ab59884, ab47431, ab49210, ab71758, ab74217, ab47465, ab27492 (Abcam); SC161HRP (Santa Cruz); PA1-14257, PA1-37483, and PA1-37484 (Thermo Scientific); 05-1049, MAB3729 (Millipore); sc-162, sc-34405, sc-161, sc-10, sc-8307, sc-46394, sc-46395, sc-81478 (Santa Cruz Biotechnology); 8198, 3127, 3148, and 4560 (Cell Signaling Technology); and 700261, 370100, 718000 (Life Technologies).

Examples of activation state-dependent antibodies that recognize phosphotyrosine residues include, but are not limited to, 4G10 Anti-Phosphotyrosine antibody from Millipore; the Anti-Phosphotyrosine antibody [PY20] (ab10321) from Abcam plc; the DELFIA Eu-N1 Anti-Phosphotyrosine P-Tyr-100, PT66, and PY20 antibodies from PerkinElmer Inc.; and the Anti-Phosphotyrosine PY20, PT-66, and PT-154 monoclonal antibodies from Sigma-Aldrich Co. Examples of activation state-dependent antibodies that recognize phosphoserine residues include, but are not limited to, PSR-45 monoclonal antibody from Sigma-Aldrich Co.; Anti-Phosphoserine antibody [PSR-45] (ab6639) from Abcam plc; Anti-Phosphoserine clone 4A4 from Millipore; Phosphoserine Antibody (NB600-558) from Novus Biologicals; the DELFIA Eu-N1 labeled anti-phosphoserine antibody from PerkinElmer Inc.; and the PhosphoSerine Antibody Q5 from Qiagen. Examples of activation state-dependent antibodies that recognize phosphothreonine residues include, but are not limited to, PTR-8 monoclonal antibody P3555 from Sigma-Aldrich Co.; Phospho-Threonine Antibody (P-Thr-Polyclonal) #9381 from Cell Signaling Technology; Anti-Phosphothreonine antibody (ab9337) from Abcam plc; and the Phospho-Threonine Antibody Q7 from Qiagen.

The term "nucleic acid" or "polynucleotide" includes deoxyribonucleotides or ribonucleotides and polymers thereof in either single- or double-stranded form such as, for example, DNA and RNA. Nucleic acids include nucleic acids containing known nucleotide analogs or modified backbone residues or linkages, which are synthetic, naturally occurring, and non-naturally occurring, and which have similar binding properties as the reference nucleic acid. Examples of such analogs include, without limitation, phosphorothioates, phosphoramidates, methyl phosphonates, chiral-methyl phosphonates, 2'-O-methyl ribonucleotides, and peptide-nucleic acids (PNAs). Unless specifically limited, the term encompasses nucleic acids containing known analogues of natural nucleotides that have similar binding properties as the reference nucleic acid. Unless otherwise indicated, a particular nucleic acid sequence also implicitly encompasses conservatively modified variants thereof and complementary sequences as well as the sequence explicitly indicated.

The term "oligonucleotide" includes a single-stranded oligomer or polymer of RNA, DNA, RNA/DNA hybrid, and/or a mimetic thereof. In certain instances, oligonucleotides are composed of naturally-occurring (i.e., unmodified) nucleobases, sugars, and internucleoside (backbone) linkages. In certain other instances, oligonucleotides comprise modified nucleobases, sugars, and/or internucleoside linkages.

As used herein, the term "mismatch motif" or "mismatch region" refers to a portion of an oligonucleotide that does not have 100% complementarity to its complementary sequence. An oligonucleotide may have at least one, two, three, four, five, six, or more mismatch regions. The mismatch regions may be contiguous or may be separated by 1, 2, 3, 4, 5, 6, 7, 8, 9, 10, 11, 12, or more nucleotides. The mismatch motifs or regions may comprise a single nucleotide or may comprise two, three, four, five, or more nucleotides.

The phrase "stringent hybridization conditions" refers to conditions under which an oligonucleotide will hybridize to its complementary sequence, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization.

The terms "substantially identical" or "substantial identity," in the context of two or more nucleic acids, refer to two or more sequences or subsequences that are the same or have a specified percentage of nucleotides that are the same (i.e., at least about 60%, preferably at least about 65%, 70%, 75%, 80%, 85%, 90%, or 95% identity over a specified region) when compared and aligned for maximum correspondence over a comparison window or designated region as measured using a sequence comparison algorithm or by manual alignment and visual inspection. This definition, when the context indicates, also refers analogously to the complement of a sequence. Preferably, the substantial identity exists over a region that is at least about 5, 10, 15, 20, 25, 30, 35, 40, 45, 50, 75, or 100 nucleotides in length.

The term "incubating" is used synonymously with "contacting" and "exposing" and does not imply any specific time or temperature requirements unless otherwise indicated.

"Receptor tyrosine kinases" or "RTKs" include a family of fifty-six (56) proteins characterized by a transmembrane domain and a tyrosine kinase motif. RTKs function in cell signaling and transmit signals regulating growth, differentiation, adhesion, migration, and apoptosis. The mutational activation and/or overexpression of receptor tyrosine kinases transforms cells and often plays a crucial role in the development of cancers. RTKs have become targets of various molecularly targeted agents such as trastuzumab, cetuximab, gefitinib, erlotinib, sunitinib, imatinib, nilotinib, and the like. One well-characterized signal transduction pathway is the MAP kinase pathway, which is responsible for transducing the signal from epidermal growth factor (EGF) to the promotion of cell proliferation in cells.

III. Description of the Embodiments

A. Methods for Therapy Selection

In certain aspects, the present invention provides methods to predicting and/or evaluating a patient's response to EGFR inhibitor therapy in a sample such as tumor tissue, circulating tumor cells (CTC), or fine needle aspirates (FNA). The methods herein provide an optimum therapeutic strategy for the patient. In other aspects, the methods provided herein find utility in selecting a combination therapy for the treatment of a malignant cancer involving aberrant EGFR and/or c-Met signaling.

The present invention provides methods for selecting a therapeutically effective anticancer drug for the treatment of patients with NSCLC. In some instance, the patient has an EGFR gene mutation. The method comprises measuring the expression and/or activation level of EGFR and cMET in a cellular extract generated from the patient's cancer cell, and calculating the EGFR/cMET index from said measurements. For instance, the EGFR/cMET index can be calculated from the expression levels of EGFR and cMET or from their activation levels. In some embodiments, the method also includes determining the EGFR mutation status of the patient. In other embodiments, the expression level of the cMET ligand, hepatocyte growth factor (HGF), is used to calculate the index instead of cMET. In yet other embodiments, the expression levels of HGF cMET are used to determine the patient's index. The expression levels and/or activated levels can be measured using the methods described in the section below.

The measured levels of the analytes can be converted into an analyte index (e.g., EGFR/cMET), which compares the levels of two particular analytes present in a single sample or equivalent samples from the patient. In some instances, the EGFR/cMET index represents a ratio that can be multiplied by a numerical factor such that the index is relative to that of a control cell line such as HCC827. In some instances, the numerical factor is about 2, 5, 10, 15, 20, 25, 30 or 35. In preferred embodiments, the numerical factor is 20.

In some embodiments, the EGFR/cMET index is calculated from the ratio of activated HER1 to activated cMET multiplied by a numerical factor. In other embodiments, the EGFR/cMET index is calculated from the ratio of total HER1 to total cMET multiplied by a numerical factor.

The EGFR/cMET index can be a numerical value between 0 to about 20 or more, e.g., 0.1, 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20 or more. In some embodiments, the EGFR/cMET index between 0 to about 12, e.g., 0.1, 0.3, 0.5, 0.7, 0.9, 1.0, 1.1, 1.3, 1.5, 1.7, 1.9, 2.0, 2.1, 2.3, 2.5, 2.7, 2.9, 3.0, 3.1, 3.3, 3.5, 3.7, 3.9, 4.0, 4.1, 4.3, 4.5, 4.7, 4.9, 5.0, 5.1, 5.3, 5.5, 5.7, 5.9, 6.0, 6.1, 6.3, 6.5, 6.7, 6.9, 7.0, 7.1, 7.3, 7.5, 7.7, 7.9, 8.0, 8.1, 8.3, 8.5, 8.7, 8.9, 9.0, 9.1, 9.3, 9.5, 9.7, 9.9, 10.0, 10.1, 10.3, 10.5, 10.7, 10.9, 11.0, 11.1, 11.3, 11.5, 11.7, 11.9 and 12.0.

Table 1 shows the expression level of total HER1 protein and total cMET protein measured by CEER™ for a representative group of NSCLC patients. The EGFR/cMET index was calculated by dividing the total HER1 level by the total cMET level and multiplying the value by the factor 20. For example, Patient A has an EGFR/cMET index of 2.28 (e.g., (100.44÷880.020)×20)=2.28).

TABLE 1

| Patient | EGFR level | cMET level | EGFR level divided by cMET level | EGFR/cMET index |
|---|---|---|---|---|
| A | 100.44 | 880.02 | 0.114139 | 2.282782 |
| B | 74.35 | 174.07 | 0.427117 | 8.542342 |
| C | 59.60 | 349.96 | 0.170306 | 3.406126 |
| D | 55.79 | 1432.94 | 0.038933 | 0.778655 |
| E | 46.07 | 799.87 | 0.0576 | 1.152005 |
| F | 7.69 | 27.59 | 0.278681 | 5.573629 |
| G | 3.14 | 117.14 | 0.026784 | 0.535674 |
| H | 108.43 | 1246.51 | 0.086985 | 1.739703 |
| I | 107.46 | 546.47 | 0.196645 | 3.93289 |
| J | 95.40 | 2000.00 | 0.047699 | 0.95397 |
| K | 74.64 | 285.44 | 0.261493 | 5.22986 |
| L | 67.00 | 197.25 | 0.339671 | 6.793421 |
| M | 65.51 | 338.60 | 0.193459 | 3.869174 |
| N | 64.59 | 319.32 | 0.202264 | 4.045276 |
| O | 51.70 | 134.96 | 0.383048 | 7.660969 |
| P | 2.28 | 8.28 | 0.275564 | 5.511272 |
| Q | 155.50 | 1234.39 | 0.125975 | 2.519497 |
| R | 170.91 | 2000.00 | 0.085455 | 1.709092 |
| S | 162.39 | 1878.38 | 0.086451 | 1.729011 |
| T | 109.36 | 304.62 | 0.359001 | 7.180015 |
| U | 41.09 | 198.91 | 0.206573 | 4.131458 |
| V | 22.53 | 301.46 | 0.074753 | 1.495069 |
| W | 22.08 | 36.38 | 0.606998 | 12.13996 |

In some embodiments, patients with an EGFR/cMET index between 2 and 20, e.g., 2.5, 3, 4, 5, 6, 7, 8, 9, 10, 11, 12, 13, 14, 15, 16, 17, 18, 19, or 20, are predicted to respond to an EGFR inhibitor and can be administered an EGFR inhibitor therapy. For instance, Patients A, B, C, F, I, K, L, M, N, O, P, Q, T, U and W (see, Table 1) are determined to be responders to EGFR inhibitor therapy. In other embodiments, patients with an EGFR/cMET index between 0 to 2, e.g., 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, or 1.9, are predicted to be resistant to an EGFR inhibitor and can be administered a cMET inhibitor therapy or a combination therapy of a cMET inhibitor and an EGFR inhibitor. Patient D, E, G, H, J, R, S and V are determined to be non-responders to EGFR inhibitor therapy. These patients may respond to cMET inhibitor therapy or cMET inhibitor combination therapy. In additional embodiments, patients are considered to be resistant to an EGFR inhibitor if the patient has a high level of activated HER3, a high level of total HER3 and/or has a HER3 gene mutation. Thus, the method provided herein can predict a patient's response or resistance to EGFR inhibitor therapy. Also, the method can be used to determine whether a patient with NSCLC would benefit from an EGFR inhibitor therapy, cMET therapy or a combination therapy.

In other embodiments, the EGFR/cMET index of a sample is compared to a reference index cut-off, wherein the reference index cut-off is empirically determined from the EGFR/cMET index of a control cell line or control patient population such as a patient responsive to EGFR inhibitor or CMET inhibitor. The reference cut-off may be a numerical value from about 1 to 20 or more, e.g., 1, 2, 3, 4, 5, 6, 7, 8, 9, 10, 11, 12, 13, 14, 15, 16, 17, 18, 19, 20 or more. In some embodiments, the reference cut-off value is 2, and thus, the patients with an EGFR/cMET index above the cut-off are predicted to be responders of EGFR inhibitor therapy and patients below the cut-off are predicted to be non-responders. In other embodiments, if the patients have an activating EGFR mutation and the reference cut-off value is 1, the patients with an EGFR/cMET index above the cut-off are predicted to be responders of EGFR inhibitor therapy and patients below the cut-off are predicted to be non-responders.

In addition, the method provided herein can be used to determine the disease status of the patient. In some embodiments, a low EGFR/cMET index represents an index value of less than the reference cut-off value, such as, less than the reference cut-off value of 2, e.g., 1.9, 1.8, 1.7, 1.6, 1.5, 1.4, 1.3, 1.2, 1.1, 1.0, 0.9, 0.8, 0.7, 0.6, 0.5, 0.4, 0.3, 0.2, 0.1 or less. In some embodiments, a high EGFR/cMET index represents an index value of greater than the reference cut-off value, e.g., greater than the reference cut-off value of 2.

In some instances, a low EGFR/cMET index between 0 and 2 can indicate that the subject has progressive disease. In other instances, a high EGFR/cMET index, such as greater than 2, e.g., 2.1, 2.3, 2.5, 2.7, 2.9, 3, 4, 5, 6, 7, 8, 9, 10, 11, 12, 13, 14, 15, 16, 17, 18, 19, 20 or more can indicate that the patient has prolonged (longer duration of survival) PFS compared to a control subject who has a low EGFR/cMET index. In some instances, prolonged progression-free survival is greater than about 5-12 months, e.g., greater than about 5, 6, 7, 8, 9, 10, 11, or 12 months. In some instances, prolonged progression-free survival corresponds to a survival rate of greater than 1 month.

In some embodiments, the method also comprises determining if the cancer cells derived from the patient have an activating EGFR mutation, such as E709D, E709Q, E709K, E709A, E709A, G719S, G719C, G719A, G719R, S768I, T790M, L858R, L858M, L861Q or L861R. The presence of an activating EGFR mutation indicates that the patient has prolonged (better) progression-free survival compared to a patient with a wild-type EGFR gene.

In some embodiments for calculating the EGFR/cMET index, the expression level of cMET is replaced by the expression level of HGF, such that the method includes determining and/or quantifying the expression of HGF. For example, the index may be calculated from the ratio of total HER1 expression to total HGF expression multiplied by a numerical factor. In other embodiments, the EGFR/cMET index includes the expression level or activation level of EGFR and cMET, as well as the expression level of HGF. For example, the index may be calculated from the ratio of total or activated HER1 to cMET multiplied by a numerical factor, combined with (e.g., added to) an HGF index derived on the expression level of HGF.

B. Methods for Monitoring a Patient's Response to Drug

The present invention provides methods for determining whether a patient who was an initial responder to EGFR inhibitor treatment has acquired drug resistance. The method comprises detecting, quantifying, and comparing the activity of EGFR and cMET, which can be represented as the patient's EGFR/cMET index over time. The index is used to determine whether the patient has acquired EGFR inhibitor resistance. The method may also be used to determine whether the patient would benefit from cMET inhibitor therapy alone or in combination with EGFR inhibitor therapy. Accordingly, knowledge of the EGFR/cMET index within a cancer cell prior to, during, and after treatment provides a physician with highly relevant information that can be used to select an appropriate course of treatment to adopt. The index provides the physician with a longitudinal evaluation of the patient's drug response.

By comparing the EGFR/cMET index of a sample taken prior to EGFR inhibitor treatment (e.g., $t_1$) to the index of a sample taken during or after treatment (e.g., $t_2$), it can be determined if the patient is responding to the therapy and/or if the patient has acquired EGFR inhibitor resistance. If the EGFR/cMET index increases from $t_1$ to $t_2$, e.g., the index is greater at $t_2$ than at $t_1$, the patient is likely to have improved (extended or prolonged) progression-free survival compared to at $t_1$. If the EGFR/cMET index decreases $t_1$ to $t_2$, e.g., the index is lower at $t_2$ than at $t_1$, the patient is predicted to have shorter progression-free survival compared to at $t_1$. The patient with shorter PFS is likely to have elevated levels of activated cMET, and also to be resistant to the EGFR inhibitor therapy.

In some embodiments, if the EGFR/cMET index of a patient's cancer cell at a time point during treatment or after treatment (e.g., $t_2$) is greater than the reference cut-off value, such as, for example, between 2 and 10, e.g., 2.1, 2.5, 2.7, 2.9, 3, 4, 5, 6, 7, 8, 9, 9.1, 9.5, 9.7 or 9.9, then the subject should be administered an EGFR inhibitor drug. And, if the EGFR/cMET index of the patient's cancer cell at $t_2$ is lower than the reference cut-off value, such as, for example, between 0 and 2, e.g., 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, or 1.9, then the patient should be administered a cMET inhibitor drug alone or in combination with an EGFR inhibitor drug.

In other embodiments, the method comprises measuring the expression level of the cMET ligand, hepatocyte growth factor (HGF), in place of measuring the expression level of cMET. Thus, the EGFR/HGF index can be calculated from the expression level of EGFR and the expression level of HGF. In yet other embodiments, an HGF index is determined independently of the EGFR/cMET index, such that the HGF index represents the expression level of HGF. In yet other embodiments, the EGFR/cMET index is calculated based on the EGFR/HGF index, or the EGFR/cMET index and the HGF index. In some embodiments, the expression level or activation level of other analytes such as HGF, HER2, HER3, IGFR1R, PI3K, and SHC can used to calculate the EGFR/cMET index.

C. Measuring Analytes

In some embodiments, the expression of various analytes is detected at the level protein expression using, for example, an immunoassay (e.g., ELISA or CEER™) or an immunohistochemical assay.

Suitable ELISA kits for determining the presence or level of an analyte in a serum, plasma, saliva, urine, tumor tissue, circulating cells, cellular extract, or FNA sample are available from, e.g., Antigenix America Inc. (Huntington Station, N.Y.), Promega (Madison, Wis.), R&D Systems, Inc. (Minneapolis, Minn.), Invitrogen (Camarillo, Calif.), CHEMICON International, Inc. (Temecula, Calif.), Neogen Corp. (Lexington, Ky.), PeproTech (Rocky Hill, N.J.), Alpco Diagnostics (Salem, N.H.), Pierce Biotechnology, Inc. (Rockford, Ill.), and/or Abazyme (Needham, Mass.).

One skilled in the art recognizes that an antibody, antibody fragment, immunoconjugate and the like that can specifically bind to (e.g., recognizes) the analyte polypeptide are useful to detect the level of protein expression of the analytes described herein.

In certain embodiments, the present invention provides methods for detecting the expression and/or activation states of EGFR and c-Met, and optionally a plurality of analytes such as HGF, HER2, HER3, HGF, PI3K, SHC, and IGF1R, in tumor cells derived from tumor tissue or circulating cells of a solid tumor in a specific, multiplex, high-throughput assay, such as CEER™. Collaborative Enzyme Enhanced Reactive ImmunoAssay (CEER™), also known as the Collaborative Proximity Immunoassay (COPIA) is described in the following patent documents which are herein incorporated by reference in their entirety for all purposes: U.S. Pat.

Nos. 8,609,349 and 8,163,499; U.S. Patent App. Publication Nos. US2008/261829, US2009/035792, US2011/071042, US2011/275097, US2011/281748, US2012/270745, US2012/277109, US2013/237436 and US2014/024548; and PCT Publication Nos., WO 2012/119113 and WO 2013/033623.

In other embodiments, the expression of various analytes is detected at the level of mRNA expression with an assay such as, for example, a hybridization assay (e.g., microarray) or an amplification-based assay. In preferred embodiments, the levels of mRNA expression of the analytes provided herein are performed by Northern blotting, Reverse Transcriptase Polymerase Chain Reaction (RT-PCR), or quantitative RT-PCR (qRT-PCR).

In some instance, the method provided herein includes detecting the presence or absence of an activating EGFR gene mutation. Various methods for identifying a gene mutation are known to those skilled in the art, such as polymerase chain reaction (PCR) based analysis, sequence analysis, and electrophoretic analysis. Some examples of suitable techniques involve but are not limited to DNA sequencing, capillary electrophoresis, hybridization, allele-specific probes or primers, single-strand conformation polymorphism analysis, nucleic acid arrays, bead arrays, restriction fragment length polymorphism analysis, cleavage fragment length polymorphism analysis, random amplified polymorphic DNA, ligase detection reaction, heteroduplex or fragment analysis, differential sequencing with mass spectrometry, atomic force microscopy, pyrosequencing, TaqMan assays (Applied Biosystems, Inc., Foster City, Calif.), Molecular Beacon (Stratagene, La Jolla, Calif.) assays, and the like.

D. Proximity Dual Detection Assays (CEER™)

Figure 11A:
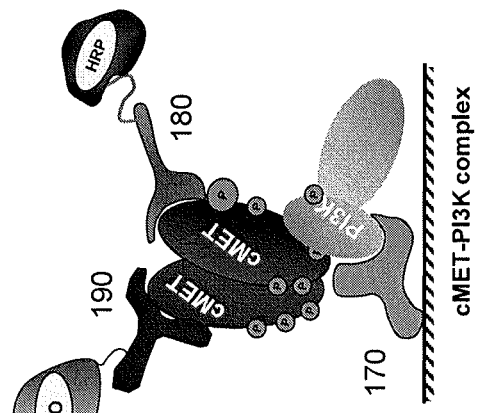
FIGS. 11A-D show exemplary embodiments of the CEER cMET assay for detecting and measuring the activated level of cMET in a sample.

In some embodiments, the assay for detecting the activation level of the cMET analyte in a cellular extract of tumor cells comprises: (1) a capture antibody 110 specific to phospho-cMET; (2) a detection antibody 120 specific for an activated form of cMET (i.e., activation state-dependent antibody); and (3) a detection antibody 130 which detects the total amount of the analyte (i.e., activation state-independent antibody) but recognizes a different epitope than detection antibody 120 (FIG. 11A).

Figure 11B:
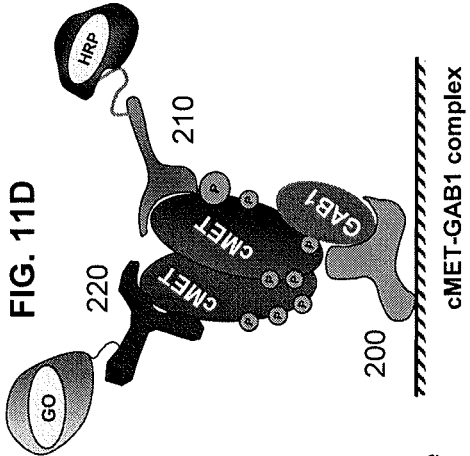

In some embodiments, the assay for detecting the activation level of the cMET analyte or a cMET homodimer in a cellular extract of tumor cells comprises: (1) a capture antibody 140 specific to phospho-cMET; (2) a detection antibody 150 which detects the total amount of the analyte (i.e., activation state-independent antibody); and (3) a detection antibody 160 which detects the total amount of the analyte (i.e., activation state-independent antibody) but recognizes a different epitope than detection antibody 150 (FIG. 11B).

Figure 11C:
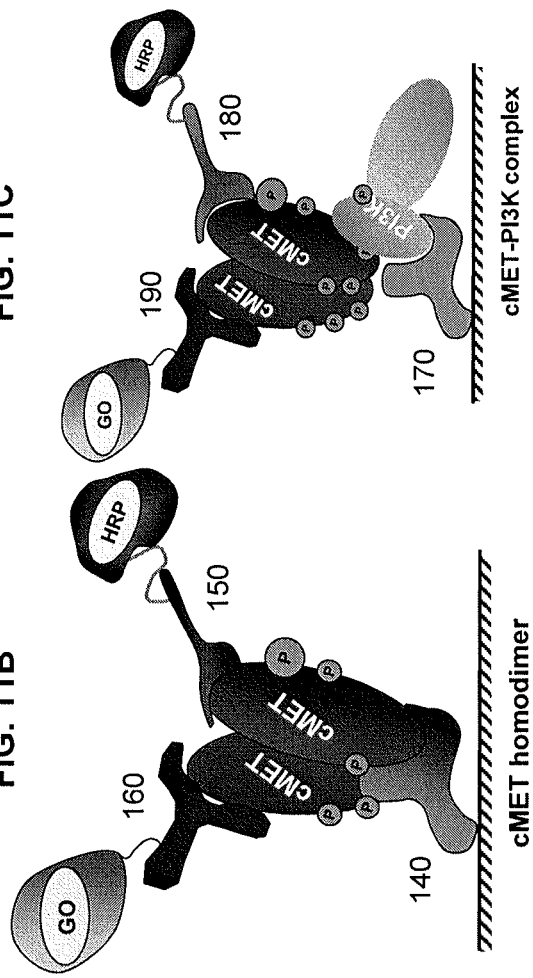

In some embodiments, the assay for detecting the activation level of the cMET analyte or a cMET-PI3K complex in a cellular extract of tumor cells comprises: (1) a capture antibody 170 specific to PI3K; (2) a detection antibody 180 which detects the total amount of the analyte (i.e., activation state-independent antibody); and (3) a detection antibody 190 which detects the total amount of the analyte (i.e., activation state-independent antibody) but recognizes a different epitope than detection antibody 180 (FIG. 11C).

Figure 11D:
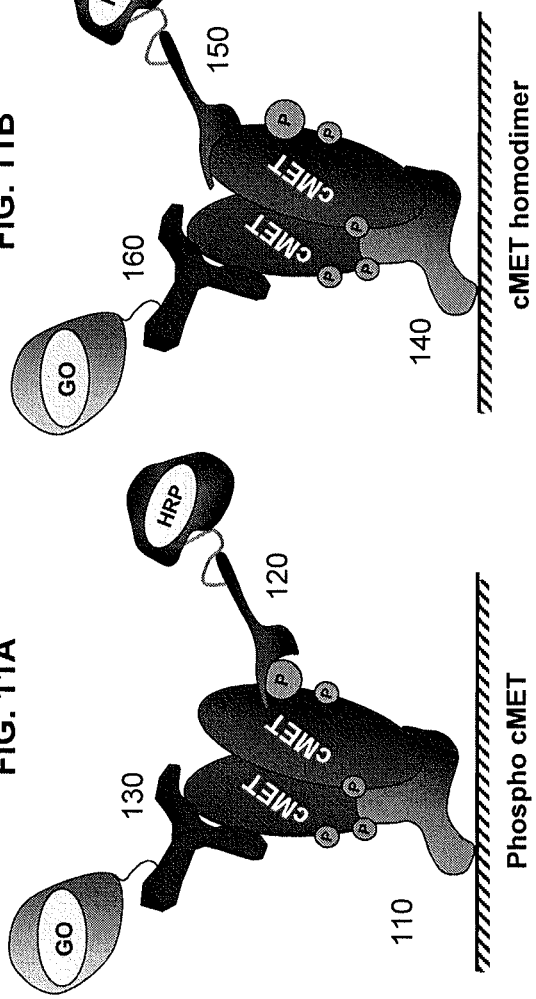

In some embodiments, the assay for detecting the activation level of the cMET analyte or a cMET-GAB1 complex in a cellular extract of tumor cells comprises: (1) a capture antibody 200 specific to GAB1; (2) a detection antibody 210 which detects the total amount of the analyte (i.e., activation state-independent antibody); and (3) a detection antibody 190 which detects the total amount of the analyte (i.e., activation state-independent antibody) but recognizes a different epitope than detection antibody 220 (FIG. 11D).

In some embodiments, the assay for detecting the expression and/or activation level of one or more analytes (e.g., one or more signal transduction molecules such as one or more components of the HER1 and/or c-Met signaling pathways) of interest in a cellular extract of cells such as tumor cells is a multiplex, high-throughput proximity (i.e., three-antibody) assay having superior dynamic range. As a non-limiting example, the three antibodies used in the proximity assay can comprise: (1) a capture antibody specific for a particular analyte of interest; (2) a detection antibody specific for an activated form of the analyte (i.e., activation state-dependent antibody); and (3) a detection antibody which detects the total amount of the analyte (i.e., activation state-independent antibody). The activation state-dependent antibody is capable of detecting, e.g., the phosphorylation, ubiquitination, and/or complexation state of the analyte, while the activation state-independent antibody is capable of detecting the total amount (i.e., both the activated and non-activated forms) of the analyte. The proximity assay described herein is also known as a Collaborative Enzyme Enhanced Reactive ImmunoAssay (CEER™) or a Collaborative Proximity Immunoassay (COPIA).

In one particular embodiment, the proximity assay for detecting the activation level or status of an analyte of interest comprises:

(i) incubating the cellular extract with one or a plurality of dilution series of capture antibodies to form a plurality of captured analytes;

(ii) incubating the plurality of captured analytes with detection antibodies comprising one or a plurality of activation state-independent antibodies and one or a plurality of activation state-dependent antibodies specific for the corresponding analytes to form a plurality of detectable captured analytes, wherein the activation state-independent antibodies are labeled with a facilitating moiety, the activation state-dependent antibodies are labeled with a first member of a signal amplification pair, and the facilitating moiety generates an oxidizing agent which channels to and reacts with the first member of the signal amplification pair;

(iii) incubating the plurality of detectable captured analytes with a second member of the signal amplification pair to generate an amplified signal; and (iv) detecting the amplified signal generated from the first and second members of the signal amplification pair.

In another particular embodiment, the proximity assay for detecting the activation level or status of an analyte of interest that is a truncated receptor comprises:

(i) incubating the cellular extract with a plurality of beads specific for an extracellular domain (ECD) binding region of a full-length receptor;

(ii) removing the plurality of beads from the cellular extract, thereby removing the full-length receptor to form a cellular extract devoid of the full-length receptor;

(iii) incubating the cellular extract devoid of the full-length receptor with one or a plurality of capture antibodies specific for an intracellular domain (ICD) binding region of the full-length receptor to form a plurality of captured truncated receptors;

(iv) incubating the plurality of captured truncated receptors with detection antibodies comprising one or a plurality of activation state-independent antibodies and one or a plurality of activation state-dependent antibodies specific for an ICD binding region of the full-length receptor to form a plurality of detectable captured truncated receptors, wherein the activation state-independent antibodies are labeled with a facilitating moiety, the activation state-dependent antibodies are labeled with a first member of a signal amplification pair, and the facilitating moiety generates an oxidizing agent which channels to and reacts with the first member of the signal amplification pair;

(v) incubating the plurality of detectable captured truncated receptors with a second member of the signal amplification pair to generate an amplified signal; and (vi) detecting the amplified signal generated from the first and second members of the signal amplification pair.

In certain embodiments, the truncated receptor is p95HER2 and the full-length receptor is HER2. In other embodiments, the truncated receptor is a truncated form of HER3 and the full-length receptor is HER3. In yet other embodiments, the truncated receptor is a truncated form of c-Met and the full-length receptor is c-Met. In further embodiments, the plurality of beads specific for an extracellular domain (ECD) binding region comprises a streptavidin-biotin pair, wherein the biotin is attached to the bead and the biotin is attached to an antibody (e.g., wherein the antibody is specific for the ECD binding region of the full-length receptor).

In alternative embodiments, the activation state-dependent antibodies can be labeled with a facilitating moiety and the activation state-independent antibodies can be labeled with a first member of a signal amplification pair.

As another non-limiting example, the three antibodies used in the proximity assay can comprise: (1) a capture antibody specific for a particular analyte of interest; (2) a first detection antibody which detects the total amount of the analyte (i.e., a first activation state-independent antibody); and (3) a second detection antibody which detects the total amount of the analyte (i.e., a second activation state-independent antibody). In preferred embodiments, the first and second activation state-independent antibodies recognize different (e.g., distinct) epitopes on the analyte.

In one particular embodiment, the proximity assay for detecting the expression level of an analyte of interest comprises:

(i) incubating the cellular extract with one or a plurality of dilution series of capture antibodies to form a plurality of captured analytes;

(ii) incubating the plurality of captured analytes with detection antibodies comprising one or a plurality of first and second activation state-independent antibodies specific for the corresponding analytes to form a plurality of detectable captured analytes, wherein the first activation state-independent antibodies are labeled with a facilitating moiety, the second activation state-independent antibodies are labeled with a first member of a signal amplification pair, and the facilitating moiety generates an oxidizing agent which channels to and reacts with the first member of the signal amplification pair;

(iii) incubating the plurality of detectable captured analytes with a second member of the signal amplification pair to generate an amplified signal; and (iv) detecting the amplified signal generated from the first and second members of the signal amplification pair.

In another particular embodiment, the proximity assay for detecting the expression level of an analyte of interest that is a truncated receptor comprises:

(i) incubating the cellular extract with a plurality of beads specific for an extracellular domain (ECD) binding region of a full-length receptor;

(ii) removing the plurality of beads from the cellular extract, thereby removing the full-length receptor to form a cellular extract devoid of the full-length receptor;

(iii) incubating the cellular extract devoid of the full-length receptor with one or a plurality of capture antibodies specific for an intracellular domain (ICD) binding region of the full-length receptor to form a plurality of captured truncated receptors;

(iv) incubating the plurality of captured truncated receptors with detection antibodies comprising one or a plurality of first and second activation state-independent antibodies specific for an ICD binding region of the full-length receptor to form a plurality of detectable captured truncated receptors, wherein the first activation state-independent antibodies are labeled with a facilitating moiety, the second activation state-independent antibodies are labeled with a first member of a signal amplification pair, and the facilitating moiety generates an oxidizing agent which channels to and reacts with the first member of the signal amplification pair;

(v) incubating the plurality of detectable captured truncated receptors with a second member of the signal amplification pair to generate an amplified signal; and (vi) detecting the amplified signal generated from the first and second members of the signal amplification pair.

In certain embodiments, the truncated receptor is a truncated form of c-MET and the full-length receptor is c-MET. In further embodiments, the plurality of beads specific for an extracellular domain (ECD) binding region comprises a streptavidin-biotin pair, wherein the biotin is attached to the bead and the biotin is attached to an antibody (e.g., wherein the antibody is specific for the ECD binding region of the full-length receptor).

In alternative embodiments, the first activation state-independent antibodies can be labeled with a first member of a signal amplification pair and the second activation state-independent antibodies can be labeled with a facilitating moiety.

The proximity assays described herein are typically antibody-based arrays which comprise one or a plurality of different capture antibodies at a range of capture antibody concentrations that are coupled to the surface of a solid support in different addressable locations.

The capture antibodies, activation state-independent antibodies, and activation state-dependent antibodies are preferably selected to minimize competition between them with respect to analyte binding (i.e., all antibodies can simultaneously bind their corresponding signal transduction molecules).

In some embodiments, activation state-independent antibodies for detecting activation levels of one or more of the analytes or, alternatively, first activation state-independent antibodies for detecting expression levels of one or more of the analytes further comprise a detectable moiety. In such instances, the amount of the detectable moiety is correlative to the amount of one or more of the analytes in the cellular extract. Examples of detectable moieties include, but are not limited to, fluorescent labels, chemically reactive labels, enzyme labels, radioactive labels, and the like. Preferably, the detectable moiety is a fluorophore such as an Alexa Fluor® dye (e.g., Alexa Fluor® 647), fluorescein, fluorescein isothiocyanate (FITC), Oregon Green™; rhodamine, Texas red, tetrarhodamine isothiocynate (TRITC), a CyDye™ fluor (e.g., Cy2, Cy3, Cy5), and the like. The detectable moiety can be coupled directly or indirectly to the activation state-independent antibodies using methods well-known in the art.

In certain instances, activation state-independent antibodies for detecting activation levels of one or more of the analytes or, alternatively, first activation state-independent antibodies for detecting expression levels of one or more of the analytes are directly labeled with the facilitating moiety. The facilitating moiety can be coupled to activation state-independent antibodies using methods well-known in the art. A suitable facilitating moiety for use in the present invention includes any molecule capable of generating an oxidizing agent which channels to (i.e., is directed to) and reacts with (i.e., binds, is bound by, or forms a complex with) another molecule in proximity (i.e., spatially near or close) to the facilitating moiety. Examples of facilitating moieties include, without limitation, enzymes such as glucose oxidase or any other enzyme that catalyzes an oxidation/reduction reaction involving molecular oxygen ($O_2$) as the electron acceptor, and photosensitizers such as methylene blue, rose bengal, porphyrins, squarate dyes, phthalocyanines, and the like. Non-limiting examples of oxidizing agents include hydrogen peroxide ($H_2O_2$), a singlet oxygen, and any other compound that transfers oxygen atoms or gains electrons in an oxidation/reduction reaction. Preferably, in the presence of a suitable substrate (e.g., glucose, light, etc.), the facilitating moiety (e.g., glucose oxidase, photosensitizer, etc.) generates an oxidizing agent (e.g., hydrogen peroxide ($H_2O_2$), single oxygen, etc.) which channels to and reacts with the first member of the signal amplification pair (e.g., horseradish peroxidase (HRP), hapten protected by a protecting group, an enzyme inactivated by thioether linkage to an enzyme inhibitor, etc.) when the two moieties are in proximity to each other.

In certain other instances, activation state-independent antibodies for detecting activation levels of one or more of the analytes or, alternatively, first activation state-independent antibodies for detecting expression levels of one or more of the analytes are indirectly labeled with the facilitating moiety via hybridization between an oligonucleotide linker conjugated to the activation state-independent antibodies and a complementary oligonucleotide linker conjugated to the facilitating moiety. The oligonucleotide linkers can be coupled to the facilitating moiety or to the activation state-independent antibodies using methods well-known in the art. In some embodiments, the oligonucleotide linker conjugated to the facilitating moiety has 100% complementarity to the oligonucleotide linker conjugated to the activation state-independent antibodies. In other embodiments, the oligonucleotide linker pair comprises at least one, two, three, four, five, six, or more mismatch regions, e.g., upon hybridization under stringent hybridization conditions. One skilled in the art will appreciate that activation state-independent antibodies specific for different analytes can either be conjugated to the same oligonucleotide linker or to different oligonucleotide linkers.

The length of the oligonucleotide linkers that are conjugated to the facilitating moiety or to the activation state-independent antibodies can vary. In general, the linker sequence can be at least about 5, 10, 15, 20, 25, 30, 35, 40, 45, 50, 75, or 100 nucleotides in length. Typically, random nucleic acid sequences are generated for coupling. As a non-limiting example, a library of oligonucleotide linkers can be designed to have three distinct contiguous domains: a spacer domain; signature domain; and conjugation domain. Preferably, the oligonucleotide linkers are designed for efficient coupling without destroying the function of the facilitating moiety or activation state-independent antibodies to which they are conjugated.

The oligonucleotide linker sequences can be designed to prevent or minimize any secondary structure formation under a variety of assay conditions. Melting temperatures are typically carefully monitored for each segment within the linker to allow their participation in the overall assay procedures. Generally, the range of melting temperatures of the segment of the linker sequence is between 1-10° C. Computer algorithms (e.g., OLIGO 6.0) for determining the melting temperature, secondary structure, and hairpin structure under defined ionic concentrations can be used to analyze each of the three different domains within each linker. The overall combined sequences can also be analyzed for their structural characterization and their comparability to other conjugated oligonucleotide linker sequences, e.g., whether they will hybridize under stringent hybridization conditions to a complementary oligonucleotide linker.

The spacer region of the oligonucleotide linker provides adequate separation of the conjugation domain from the oligonucleotide crosslinking site. The conjugation domain functions to link molecules labeled with a complementary oligonucleotide linker sequence to the conjugation domain via nucleic acid hybridization. The nucleic acid-mediated hybridization can be performed either before or after antibody-analyte (i.e., antigen) complex formation, providing a more flexible assay format. Unlike many direct antibody conjugation methods, linking relatively small oligonucleotides to antibodies or other molecules has minimal impact on the specific affinity of antibodies towards their target analyte or on the function of the conjugated molecules.

In some embodiments, the signature sequence domain of the oligonucleotide linker can be used in complex multiplexed protein assays. Multiple antibodies can be conjugated with oligonucleotide linkers with different signature sequences. In multiplex immunoassays, reporter oligonucleotide sequences labeled with appropriate probes can be used to detect cross-reactivity between antibodies and their antigens in the multiplex assay format.

Oligonucleotide linkers can be conjugated to antibodies or other molecules using several different methods. For example, oligonucleotide linkers can be synthesized with a thiol group on either the 5' or 3' end. The thiol group can be deprotected using reducing agents (e.g., TCEP-HCl) and the resulting linkers can be purified by using a desalting spin column. The resulting deprotected oligonucleotide linkers can be conjugated to the primary amines of antibodies or other types of proteins using heterobifunctional cross linkers such as SMCC. Alternatively, 5'-phosphate groups on oligonucleotides can be treated with water-soluble carbodiimide EDC to form phosphate esters and subsequently coupled to amine-containing molecules. In certain instances, the diol on the 3'-ribose residue can be oxidized to aldehyde groups and then conjugated to the amine groups of antibodies or other types of proteins using reductive amination. In certain other instances, the oligonucleotide linker can be synthesized with a biotin modification on either the 3' or 5' end and conjugated to streptavidin-labeled molecules.

Oligonucleotide linkers can be synthesized using any of a variety of techniques known in the art, such as those described in Usman et al., *J Am. Chem. Soc.*, 109:7845 (1987); Scaringe et al., *Nucl. Acids Res.*, 18:5433 (1990);

Wincott et al., *Nucl. Acids Res.*, 23:2677-2684 (1995); and Wincott et al., *Methods Mol. Bio.*, 74:59 (1997). In general, the synthesis of oligonucleotides makes use of common nucleic acid protecting and coupling groups, such as dimethoxytrityl at the 5'-end and phosphoramidites at the 3'-end. Suitable reagents for oligonucleotide synthesis, methods for nucleic acid deprotection, and methods for nucleic acid purification are known to those of skill in the art.

In certain instances, activation state-dependent antibodies for detecting activation levels of one or more of the analytes or, alternatively, second activation state-independent antibodies for detecting expression levels of one or more of the analytes are directly labeled with the first member of the signal amplification pair. The signal amplification pair member can be coupled to activation state-dependent antibodies to detect activation levels or second activation state-independent antibodies to detect expression levels using methods well-known in the art. In certain other instances, activation state-dependent antibodies or second activation state-independent antibodies are indirectly labeled with the first member of the signal amplification pair via binding between a first member of a binding pair conjugated to the activation state-dependent antibodies or second activation state-independent antibodies and a second member of the binding pair conjugated to the first member of the signal amplification pair. The binding pair members (e.g., biotin/streptavidin) can be coupled to the signal amplification pair member or to the activation state-dependent antibodies or second activation state-independent antibodies using methods well-known in the art. Examples of signal amplification pair members include, but are not limited to, peroxidases such horseradish peroxidase (HRP), catalase, chloroperoxidase, cytochrome c peroxidase, eosinophil peroxidase, glutathione peroxidase, lactoperoxidase, myeloperoxidase, thyroid peroxidase, deiodinase, and the like. Other examples of signal amplification pair members include haptens protected by a protecting group and enzymes inactivated by thioether linkage to an enzyme inhibitor.

In one example of proximity channeling, the facilitating moiety is glucose oxidase (GO) and the first member of the signal amplification pair is horseradish peroxidase (HRP). When the GO is contacted with a substrate such as glucose, it generates an oxidizing agent (i.e., hydrogen peroxide ($H_2O_2$)). If the HRP is within channeling proximity to the GO, the $H_2O_2$ generated by the GO is channeled to and complexes with the HRP to form an HRP-$H_2O_2$ complex, which, in the presence of the second member of the signal amplification pair (e.g., a chemiluminescent substrate such as luminol or isoluminol or a fluorogenic substrate such as tyramide (e.g., biotin-tyramide), homovanillic acid, or 4-hydroxyphenyl acetic acid), generates an amplified signal. Methods of using GO and HRP in a proximity assay are described in, e.g., Langry et al., U.S. Dept. of Energy Report No. UCRL-ID-136797 (1999). When biotin-tyramide is used as the second member of the signal amplification pair, the HRP-$H_2O_2$ complex oxidizes the tyramide to generate a reactive tyramide radical that covalently binds nearby nucleophilic residues. The activated tyramide is either directly detected or detected upon the addition of a signal-detecting reagent such as, for example, a streptavidin-labeled fluorophore or a combination of a streptavidin-labeled peroxidase and a chromogenic reagent. Examples of fluorophores suitable for use in the present invention include, but are not limited to, an Alexa Fluor® dye (e.g., Alexa Fluor® 555), fluorescein, fluorescein isothiocyanate (FITC), Oregon Green™; rhodamine, Texas red, tetrarhodamine isothiocynate (TRITC), a CyDye™ fluor (e.g., Cy2, Cy3, Cy5), and the like. The streptavidin label can be coupled directly or indirectly to the fluorophore or peroxidase using methods well-known in the art. Non-limiting examples of chromogenic reagents suitable for use in the present invention include 3,3',5,5'-tetramethylbenzidine (TMB), 3,3'-diaminobenzidine (DAB), 2,2'-azino-bis(3-ethylbenzothiazoline-6-sulfonic acid) (ABTS), 4-chloro-1-napthol (4CN), and/or porphyrinogen.

In some embodiments, the glucose oxidase (GO) and the detection antibodies (e.g., activation state-independent antibodies) can be conjugated to a sulfhydryl-activated dextran molecule as described in, e.g., U.S. Pat. Nos. 8,609,349 and 8,163,499, the disclosures of which are herein incorporated by reference in their entirety for all purposes. The sulfhydryl-activated dextran molecule typically has a molecular weight of about 500 kDa (e.g., about 250, 300, 350, 400, 450, 500, 550, 600, 650, 700, or 750 kDa). In certain other embodiments, the horseradish peroxidase (HRP) and the detection antibodies (e.g., activation state-dependent antibodies) can be conjugated to a sulfhydryl-activated dextran molecule. The sulfhydryl-activated dextran molecule typically has a molecular weight of about 70 kDa (e.g., about 40, 45, 50, 55, 60, 65, 70, 75, 80, 85, 90, 95, or 100 kDa).

In another example of proximity channeling, the facilitating moiety is a photosensitizer and the first member of the signal amplification pair is a large molecule labeled with multiple haptens that are protected with protecting groups that prevent binding of the haptens to a specific binding partner (e.g., ligand, antibody, etc.). For example, the signal amplification pair member can be a dextran molecule labeled with protected biotin, coumarin, and/or fluorescein molecules. Suitable protecting groups include, but are not limited to, phenoxy-, analino-, thioether-, and selenoether-protecting groups. Additional photosensitizers and protected hapten molecules suitable for use in the proximity assays of the present invention are described in U.S. Pat. No. 5,807,675. When the photosensitizer is excited with light, it generates an oxidizing agent (i.e., singlet oxygen). If the hapten molecules are within channeling proximity to the photosensitizer, the singlet oxygen generated by the photosensitizer is channeled to and reacts with thioethers on the protecting groups of the haptens to yield carbonyl groups (ketones or aldehydes) and sulphinic acid, releasing the protecting groups from the haptens. The unprotected haptens are then available to specifically bind to the second member of the signal amplification pair (e.g., a specific binding partner that can generate a detectable signal). For example, when the hapten is biotin, the specific binding partner can be an enzyme-labeled streptavidin. Exemplary enzymes include alkaline phosphatase, β-galactosidase, HRP, etc. After washing to remove unbound reagents, the detectable signal can be generated by adding a detectable (e.g., fluorescent, chemiluminescent, chromogenic, etc.) substrate of the enzyme and detected using suitable methods and instrumentation known in the art. Alternatively, the detectable signal can be amplified using tyramide signal amplification and the activated tyramide either directly detected or detected upon the addition of a signal-detecting reagent as described above.

In yet another example of proximity channeling, the facilitating moiety is a photosensitizer and the first member of the signal amplification pair is an enzyme-inhibitor complex. The enzyme and inhibitor (e.g., phosphonic acid-labeled dextran) are linked together by a cleavable linker (e.g., thioether). When the photosensitizer is excited with light, it generates an oxidizing agent (i.e., singlet oxygen). If the enzyme-inhibitor complex is within channeling proximity to the photosensitizer, the singlet oxygen generated by the photosensitizer is channeled to and reacts with the cleavable linker, releasing the inhibitor from the enzyme, thereby activating the enzyme. An enzyme substrate is added to generate a detectable signal, or alternatively, an amplification reagent is added to generate an amplified signal.

In a further example of proximity channeling, the facilitating moiety is HRP, the first member of the signal amplification pair is a protected hapten or an enzyme-inhibitor complex as described above, and the protecting groups comprise p-alkoxy phenol. The addition of phenylenediamine and $H_2O_2$ generates a reactive phenylene diimine which channels to the protected hapten or the enzyme-inhibitor complex and reacts with p-alkoxy phenol protecting groups to yield exposed haptens or a reactive enzyme. The amplified signal is generated and detected as described above (see, e.g., U.S. Pat. Nos. 5,532,138 and 5,445,944).

An exemplary protocol for performing the proximity assays described herein (e.g., CEER™) is provided in U.S. Pat. Nos. 8,609,349 and 8,163,499, the disclosures of which are herein incorporated by reference in their entirety for all purposes.

In another embodiment, the present invention provides kits for performing the proximity assays described above comprising: (a) a dilution series of one or a plurality of capture antibodies restrained on a solid support; and (b) one or a plurality of detection antibodies (e.g., a combination of activation state-independent antibodies and activation state-dependent antibodies for detecting activation levels and/or a combination of first and second activation state-independent antibodies for detecting expression levels). In some instances, the kits can further contain instructions for methods of using the kit to detect the expression and/or activation status of one or a plurality of signal transduction molecules of cells such as tumor cells. The kits may also contain any of the additional reagents described above with respect to performing the specific methods of the present invention such as, for example, first and second members of the signal amplification pair, tyramide signal amplification reagents, substrates for the facilitating moiety, wash buffers, etc.

E. Anticancer Therapy

In some embodiments, the EGFR inhibitor therapy is an EGFR inhibitor, a pan-HER inhibitor, or combinations thereof. Non-limiting examples of EGFR inhibitors include Cetaximab, Panitumumab, Matuzumab, Nimotuzumab, ErbB1 vaccine, Erlotinib, Gefitinib, ARRY-334543, AEE788, BIBW 2992, EKB 569, CL-387-785, CUDC-101, AV-412, and combinations thereof. Non-limiting examples of pan-HER inhibitors include PF-00299804, neratinib (HKI-272), AC480 (BMS-599626), BMS-690154, PF-02341066, HM781-36B, CI-1033, BIBW-2992, and combinations thereof.

A number of therapeutic strategies have been employed to inhibit cMet, such as monoclonal antibodies and small-molecule tyrosine kinase inhibitors. Examples of cMet inhibitors under development include neutralizing antibodies, such as MAG102 (Amgen) and MetMab (Roche), as well as tyrosine kinase inhibitors (TKIs), such as ARQ197, XL184, PF-02341066, GSK1363089/XL880, MP470, MGCD265, SGX523, PF04217903 JNJ38877605, INCB28060, AMG-458, E7050, MK-2461, and BMS-777607. It has been demonstrated that cMET and HGF/SF are markers of positive response to cMET inhibitors (see, ARQ127 Study in MetMab, European Society for Medical Oncology Congress, Oct. 17, 2010). Yet interestingly, patients with a malignancy (e.g., gastric cancer) and cMet gene amplification do not respond to tyrosine kinase inhibitors. Engelman et al. (*Science*, 316:1039-1043, (2007)) demonstrated that resistance to the EGFR TKI gefitinib is associated with activated cMet which activates HER3 and the PI3K-AKT signaling pathway. Resistance to cMET and/or EGFR inhibitors may be attributed to functional redundancies among multiple signaling pathways. Thus, in many cases, there is a need to employ multi-targeted therapies to overcome resistance to tyrosine kinase inhibitors and to effectively treat malignancies involving aberrant cMet signaling.

In particular embodiments, the therapy comprises treatment with a cMet inhibitor. Non-limiting examples of compounds that modulate cMet activity are described herein and include monoclonal antibodies, small molecule inhibitors, and combinations thereof. In preferred embodiments, the cMet-modulating compound inhibits cMet activity and/or blocks cMet signaling, e.g., is a cMet inhibitor. Examples of eMet inhibitors include, but are not limited to, monoclonal antibodies such as AV299, L2G7, AMG102, DN30, OA-5D5, and MetMAb; and small molecule inhibitors of cMet such as ARQ197, AMG458, BMS-777607, XL 184, XL880, INCB28060, E7050, GSK1363089/XL880, K252a, LY2801653, MP470, MGCD265, MK-2461, NK2, NK4, SGX523, SUI 1274, SU5416, PF-04217903, PF-02341066, PHA-665752, JNJ-38877605; and combinations thereof.

In certain embodiments, the antibody such as a HGF- or c-Met-specific antibody prevents ligand/receptor binding, resulting in growth inhibition and tumor regression by inhibiting proliferation and enhancing apoptosis. In some instances, a combination of monoclonal antibodies can also be used. The strategy of using monoclonal antibodies allows for exclusive specificity against HGF/c-Met, a relatively long half-life compared to small molecule kinase inhibitors, and the potential to elicit a host immune response against tumor cells. AMG102 is a fully human IgG2 monoclonal antibody that selectively binds and neutralizes HGF, thereby preventing its binding to c-Met and subsequent activation. AMG102 has been shown to enhance the effects of various standard chemotherapeutic agents such as temozolomide and docetaxel in vitro and in xenografts when combined. MetMAb is a humanized, monovalent, antagonistic anti-c-Met antibody derived from the agonistic monoclonal antibody 5D5. MetMAb binds to c-Met with high affinity and remains on the cell surface with c-Met, preventing HGF binding and subsequent c-Met phosphorylation as well as downstream signaling activity and cellular responses. Recent preclinical studies show that MetMAb is a potent anti-c-Met inhibitor that has promise as a therapeutic antibody in human cancer, especially in combination with EGFR and/or VEGF inhibitors.

Small molecule inhibitors of c-Met include, but are not limited to, ARQ197 (ArQule), which is a non-ATP-competitive agent highly selective for the c-Met receptor. Other selective c-Met inhibitors have recently entered initial clinical evaluations and include: JNJ-38877605 (Johnson & Johnson), which is a small-molecule, ATP-competitive inhibitor of the catalytic activity of c-Met; PF-04217903 (Pfizer), which is an orally available, ATP-competitive small-molecule inhibitor of c-Met with selectivity of >1000-fold for c-Met compared with a screening panel of >150 protein kinases; SGX523 (SGX Pharmaceuticals), which is another highly selective, ATP-competitive inhibitor of c-Met with >1,000-fold selectivity for c-Met over all other kinases in a screening panel of 213 protein kinases and potent antitumor activity when dosed orally in human xenograft models with no overt toxicity.

GSK 1363089/XL880 (Exelixis) is another example of a small molecule inhibitor of c-Met which targets c-Met at an IC50 of 0.4 nM. Binding affinity is high to both c-Met and VEGFR2, causing a conformational change in the kinase to move XL880 deeper into the ATP-binding pocket. The time on target is >24 hours for both receptors. XL880 has good oral bioavailability, and it is a CYP450 substrate, but not an inhibitor or inducer. Two Phase I clinical trials examined different administration schedules of XL880, either on a 5 day on/9 day off schedule (Study 1) or as a fixed daily dose (Study 2). XL880 acts on two cooperating pathways for proliferation and survival at different points in time, already providing a therapeutic solution for tumor response to the initial assault on tumor angiogenesis. Phase II trials have started in multiple tumor types, including papillary renal cancer, gastric cancer, and head and neck cancers.

XL184 (Exelixis) is a novel, orally administered, small molecule anticancer compound that, in preclinical models, has demonstrated potent inhibition of both c-Met and VEGFR2. MP470 (SuperGen) is a novel, orally bioavailable small molecule with inhibitory activity against c-Met as well as several other protein tyrosine kinase targets, including mutant forms of c-Kit, mutant PDGFRa, and mutant Flt-3. MGCD265 (Methylgene) potently inhibits c-Met, Ron, VEGFRs, and Tie-2 enzymatic activities in vitro and has been reported to abrogate HGF dependent cellular endpoints, such as cell scatter and wound healing, as well as VEGF-dependent responses such as in vitro angiogenesis and in vivo vascular permeability. MK-2461 (Merck) is a potent inhibitor of c-Met, KDR, FGFR1/2/3, and Flt 1/3/4 that is especially active in preclinical models with MET gene amplification, in which c-Met is constitutively phosphorylated. MK-2461 has been well tolerated in early Phase I evaluation.

In certain instances, binding of HGF ligand to the c-Met receptor can be inhibited by subregions of HGF or c-Met that can act as decoys or antagonists. These decoys and antagonists stoichiometrically compete with the ligand or receptor without leading to c-Met activation, thereby preventing activation of downstream pathways and biological outcomes. Several HGF and c-Met variants have been validated experimentally as antagonists both in vitro and in vivo and work by blocking ligand binding or preventing c-Met dimerization. In addition, molecular analogs to HGF that have been shown to compete with HGF for c-Met binding have been developed.

In other embodiments, the cMet inhibitor is selected from a group consisting of a multi-kinase inhibitor, a tyrosine kinase inhibitor, and a monoclonal antibody. In particular aspects, a multi-kinase inhibitor (e.g., pan-HER inhibitor) is an agent that blocks a plurality of kinases, such as, but not limited to, cMet, RON, EGFR, HER2, HER3, VEGFR1, VEGR2, VEGFR3, PI3K, SHC, p95HER2, IGF-1R, and c-Kit. In other aspects, a tyrosine kinase inhibitor is an agent that blocks one or more tyrosine kinases such as, but not limited to, cMet, RON, EGFR, HER2, HER3, VEGFR1, VEGR2, and/or VEGFR3. Non-limiting examples of small molecule tyrosine kinase inhibitors which can be used in the present invention include a gefitinib (Iressa), erlotinib (Tarceva®), pelitinib, CP-654577, CP-724714, canertinib (CI 1033), HKI-272, lapatinib (GW-572016; Tykerb®), PKI-166, AEE788, BMS-599626, HKI-357, BIBW 2992, ARRY-334543, JNJ-26483327, and JNJ-26483327; and combinations thereof. Non-limiting examples of monoclonal antibodies for use in the present invention include trastuzumab (Herceptin®), pertuzumab (2C4), alemtuzumab (Campath®), bevacizumab (Avastin®), cetuximab (Erbitux®), gemtuzamab (Mylotarg®), panitumumab (Vectibix™), rituximab (Rituxan®), and tositumomab (BEXXAR®), and combinations thereof.

F. Methods of Administration

According to the methods of the present invention, the anticancer drugs described herein are administered to a subject by any convenient means known in the art. The methods of the present invention can be used to select a suitable anticancer drug or combination of anticancer drugs for the treatment of a tumor, e.g., non-small cell lung cancer tumor, in a subject. The methods of the present invention can also be used to identify the response of a tumor, e.g., non-small cell lung cancer tumor, in a subject to treatment with an anticancer drug or combination of anticancer drugs. In addition, the methods of the present invention can be used to predict the response of a subject having a tumor, e.g., non-small cell lung cancer tumor, to treatment with an anticancer drug or combination of anticancer drugs. The methods of the present invention can also be used to monitor the status of a tumor, e.g., non-small cell lung cancer tumor, in a subject or to monitor how a patient with the tumor is responding to treatment with an anticancer drug or combination of anticancer drugs. One skilled in the art will appreciate that the anticancer drugs described herein can be administered alone or as part of a combined therapeutic approach with conventional chemotherapy, radiotherapy, hormonal therapy, immunotherapy, and/or surgery.

In certain embodiments, the anticancer drug comprises an anti-signaling agent (i.e., a cytostatic drug) such as a monoclonal antibody or a tyrosine kinase inhibitor; an anti-proliferative agent; a chemotherapeutic agent (i.e., a cytotoxic drug); a hormonal therapeutic agent; a radiotherapeutic agent; a vaccine; and/or any other compound with the ability to reduce or abrogate the uncontrolled growth of aberrant cells such as cancerous cells. In some embodiments, the subject is treated with one or more anti-signaling agents, anti-proliferative agents, and/or hormonal therapeutic agents in combination with at least one chemotherapeutic agent. Exemplary monoclonal antibodies, tyrosine kinase inhibitors, anti-proliferative agents, chemotherapeutic agents, hormonal therapeutic agents, radiotherapeutic agents, and vaccines are described above.

In some embodiments, the anticancer drugs described herein can be co-administered with conventional immunotherapeutic agents including, but not limited to, immunostimulants (e.g., Bacillus Calmette-Guérin (BCG), levamisole, interleukin-2, alpha-interferon, etc.), immunotoxins (e.g., anti-CD33 monoclonal antibody-calicheamicin conjugate, anti-CD22 monoclonal antibody-pseudomonas exotoxin conjugate, etc.), and radioimmunotherapy (e.g., anti-CD20 monoclonal antibody conjugated to $^{111}$In, $^{90}$Y, or $^{131}$I, etc.).

Anticancer drugs can be administered with a suitable pharmaceutical excipient as necessary and can be carried out via any of the accepted modes of administration. Thus, administration can be, for example, oral, buccal, sublingual, gingival, palatal, intravenous, topical, subcutaneous, transcutaneous, transdermal, intramuscular, intra-joint, parenteral, intra-arteriole, intradermal, intraventricular, intracranial, intraperitoneal, intravesical, intrathecal, intralesional, intranasal, rectal, vaginal, or by inhalation. By "co-administer" it is meant that an anticancer drug is administered at the same time, just prior to, or just after the administration of a second drug (e.g., another anticancer drug, a drug useful for reducing the side-effects associated with anticancer drug therapy, a radiotherapeutic agent, a hormonal therapeutic agent, an immunotherapeutic agent, etc.).

A therapeutically effective amount of an anticancer drug may be administered repeatedly, e.g., at least 2, 3, 4, 5, 6, 7, 8, or more times, or the dose may be administered by continuous infusion. The dose may take the form of solid, semi-solid, lyophilized powder, or liquid dosage forms, such as, for example, tablets, pills, pellets, capsules, powders, solutions, suspensions, emulsions, suppositories, retention enemas, creams, ointments, lotions, gels, aerosols, foams, or the like, preferably in unit dosage forms suitable for simple administration of precise dosages.

As used herein, the term "unit dosage form" refers to physically discrete units suitable as unitary dosages for human subjects and other mammals, each unit containing a predetermined quantity of an anticancer drug calculated to produce the desired onset, tolerability, and/or therapeutic effects, in association with a suitable pharmaceutical excipient (e.g., an ampoule). In addition, more concentrated dosage forms may be prepared, from which the more dilute unit dosage forms may then be produced. The more concentrated dosage forms thus will contain substantially more than, e.g., at least 1, 2, 3, 4, 5, 6, 7, 8, 9, 10, or more times the amount of the anticancer drug.

Methods for preparing such dosage forms are known to those skilled in the art (see, e.g., REMINGTON'S PHARMACEUTICAL SCIENCES, 18TH ED., Mack Publishing Co., Easton, Pa. (1990)). The dosage forms typically include a conventional pharmaceutical carrier or excipient and may additionally include other medicinal agents, carriers, adjuvants, diluents, tissue permeation enhancers, solubilizers, and the like. Appropriate excipients can be tailored to the particular dosage form and route of administration by methods well known in the art (see, e.g., REMINGTON'S PHARMACEUTICAL SCIENCES, supra).

Examples of suitable excipients include, but are not limited to, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline, syrup, methylcellulose, ethylcellulose, hydroxypropylmethylcellulose, and polyacrylic acids such as Carbopols, e.g., Carbopol 941, Carbopol 980, Carbopol 981, etc. The dosage forms can additionally include lubricating agents such as talc, magnesium stearate, and mineral oil; wetting agents; emulsifying agents; suspending agents; preserving agents such as methyl-, ethyl-, and propyl-hydroxy-benzoates (i.e., the parabens); pH adjusting agents such as inorganic and organic acids and bases; sweetening agents; and flavoring agents. The dosage forms may also comprise biodegradable polymer beads, dextran, and cyclodextrin inclusion complexes.

For oral administration, the therapeutically effective dose can be in the form of tablets, capsules, emulsions, suspensions, solutions, syrups, sprays, lozenges, powders, and sustained-release formulations. Suitable excipients for oral administration include pharmaceutical grades of mannitol, lactose, starch, magnesium stearate, sodium saccharine, talcum, cellulose, glucose, gelatin, sucrose, magnesium carbonate, and the like.

In some embodiments, the therapeutically effective dose takes the form of a pill, tablet, or capsule, and thus, the dosage form can contain, along with an anticancer drug, any of the following: a diluent such as lactose, sucrose, dicalcium phosphate, and the like; a disintegrant such as starch or derivatives thereof; a lubricant such as magnesium stearate and the like; and a binder such a starch, gum acacia, polyvinylpyrrolidone, gelatin, cellulose and derivatives thereof. An anticancer drug can also be formulated into a suppository disposed, for example, in a polyethylene glycol (PEG) carrier.

Liquid dosage forms can be prepared by dissolving or dispersing an anticancer drug and optionally one or more pharmaceutically acceptable adjuvants in a carrier such as, for example, aqueous saline (e.g., 0.9% w/v sodium chloride), aqueous dextrose, glycerol, ethanol, and the like, to form a solution or suspension, e.g., for oral, topical, or intravenous administration. An anticancer drug can also be formulated into a retention enema.

For topical administration, the therapeutically effective dose can be in the form of emulsions, lotions, gels, foams, creams, jellies, solutions, suspensions, ointments, and transdermal patches. For administration by inhalation, an anticancer drug can be delivered as a dry powder or in liquid form via a nebulizer. For parenteral administration, the therapeutically effective dose can be in the form of sterile injectable solutions and sterile packaged powders. Preferably, injectable solutions are formulated at a pH of from about 4.5 to about 7.5.

The therapeutically effective dose can also be provided in a lyophilized form. Such dosage forms may include a buffer, e.g., bicarbonate, for reconstitution prior to administration, or the buffer may be included in the lyophilized dosage form for reconstitution with, e.g., water. The lyophilized dosage form may further comprise a suitable vasoconstrictor, e.g., epinephrine. The lyophilized dosage form can be provided in a syringe, optionally packaged in combination with the buffer for reconstitution, such that the reconstituted dosage form can be immediately administered to a subject.

A subject can also be monitored at periodic time intervals to assess the efficacy of a certain therapeutic regimen. For example, the activation states of certain signal transduction molecules may change based on the therapeutic effect of treatment with one or more of the anticancer drugs described herein. The subject can be monitored to assess response and understand the effects of certain drugs or treatments in an individualized approach. Additionally, subjects who initially respond to a specific anticancer drug or combination of anticancer drugs may become refractory to the drug or drug combination, indicating that these subjects have developed acquired drug resistance. These subjects can be discontinued on their current therapy and an alternative treatment prescribed in accordance with the methods of the present invention.

IV. Examples

The following examples are offered to illustrate, but not to limit, the claimed invention.

Example 1

EGFR and cMET Levels in Developing Resistance to EGFR Inhibitors in NSCLC Patients Background: Lung cancer remains clinically challenging to treat. Patients with lung cancer have an overall 5-year survival rate of 15%. It has been determined that pathway dysregulations due genetic and epigenetic alterations can alter the critical balance in numerous signal transduction pathways, thereby leading to lung cancer. Various targeted therapies directed to different key signal transduction components have been utilized in clinical trials and have yielded some positive results. For instance, tyrosine kinase inhibitors directed to EGFR, such as erlotinib and gefitinib, are approved by the U.S. Food and Drug Administration for use in previously treated non-small cell lung cancer (NSCLC). However, there remains an urgent need for methods of selecting an appropriate therapy for the treatment of NSCLC patients.

Method & Objectives: Longitudinal endoscopic ultrasound guided fine needle aspirates (FNAs) were collected from 44 NSCLC patients enrolled in a study involving EGFR inhibitors (EGFRi), such as gefitinib, erlotinib and afatinib. The patients were administered a course of EGFR inhibitor treatment and samples were taken prior to treatment (sample A), at 4 weeks into the treatment course (sample B), and at the end of the treatment course (sample C). The level of expression and activation of EGFR as well as other various receptor tyrosine kinases (RTKs, i.e., HER1, HER2, HER3, cMET, IGF1R, SHC, ALK (anaplastic lymphoma kinase), and the like) and downstream AKT and MAPK pathway proteins were measured using a triple-antibody-enzyme-channeling multiplexed protein microarray platform or CEER™. The analysis was performed in order to: 1) compare the objective response rate according to the expression/activation of RTK and pathway proteins; 2) evaluate the modulation of the RTK and pathway proteins during the treatment of EGFRi; and 3) correlate the presence of activating EGFR gene mutations and RTK activation in patients treated with EGFRi.

Results: The total expression and/or activation (e.g., phosphorylation) levels of the various analytes such as EGFR (HER1), HER2, HER3, cMET, IGF1R, SHC, PI3K, and CK (a control analyte) were measured and are presented in Tables 2 and 3. The levels are given as the calculated number of specific RTK molecules in each sample (e.g., CU/µg of sample). The presence of an EGFR gene mutation was also determined. The majority (about 75%) of the patients in the study over-expressed EGFR. FIG. 1 shows the expression level of a specific analyte (e.g., HER1, HER2, HER3, cMET, IGF1R, and PI3K) as a ratio relative to CK expression in patients carrying an EGFR gene mutation or a wild-type EGFR gene. Similarly, FIG. 2 shows the expression level of the same analytes as a ratio relative to PI3K expression in the same patient. 3 patients expressed high levels of ALK as assayed by immunohistochemistry. Varying and significant levels of cMET and HER3 were quantitated in all patients sampled.

TABLE 2

Levels of total expression of various analytes and HER1/cMET index.

| Patient No. | EGFR mut | ALK IHC | HER1 | HER2 | HER3 | cMET | HER1/cMET | HER1/cMET index |
|---|---|---|---|---|---|---|---|---|
| 10C4-006-006A | WT | POS | 171.33 | 3115.19 | 306.21 | 1531.44 | 0.11 | 2.20 |
| 10C4-006-038A | WT | NA | 76.58 | 852.68 | 11.84 | 2000.00 | 0.038 | 0.76 |
| 10C4-006-016A | WT | POS | 67.36 | 1208.48 | 41.45 | 479.20 | 0.14 | 2.80 |
| 10C4-006-004A | WT | NA | 60.61 | 193.40 | L | 180.10 | 0.337 | 6.74 |
| 10C4-006-046A | WT | NEG | 59.38 | 435.50 | 9.55 | 556.16 | 0.107 | 2.14 |
| 10C4-006-014B | WT | NA | 51.73 | 315.75 | L | 387.31 | 0.134 | 2.68 |
| 10C4-006-014A | WT | NA | 51.19 | 336.86 | 16.05 | 473.64 | 0.108 | 2.16 |
| 10C4-006-039A | WT | NA | 46.35 | 520.72 | L | 1042.02 | 0.044 | 0.89 |
| 10C4-006-014C | WT | NA | 36.42 | 275.95 | L | 432.48 | 0.084 | 1.68 |
| 10C4-006-018A | WT | POS | 0.53 | L | L | L | L | L |
| 10C4-006-029A | MUT | NA | 193.33 | 1781.91 | 27.67 | 691.55 | 0.28 | 5.59 |
| 10C4-006-031A | MUT | NA | 100.44 | 1062.08 | L | 880.02 | 0.11 | 2.28 |
| 10C4-006-003A | MUT | NA | 74.35 | 257.23 | 15.51 | 174.07 | 0.43 | 8.54 |
| 10C4-006-002A | MUT | NEG | 59.60 | 1108.77 | L | 349.96 | 0.17 | 3.41 |
| 10C4-006-028A | MUT | NEG | 55.79 | 1229.93 | 37.01 | 1432.94 | 0.04 | 0.78 |
| 10C4-006-037A | MUT | NA | 46.07 | 537.07 | 15.71 | 799.87 | 0.06 | 1.15 |
| 10C4-006-041A | MUT | NEG | 7.69 | 106.45 | L | 27.59 | 0.28 | 5.57 |
| 10C4-006-037C | MUT | NA | 3.14 | 28.98 | L | 117.14 | 0.03 | 0.54 |
| 10C4-006-021A | MUT | NEG | 0.46 | L | L | L | L | L |
| 10C4-006-044A | MUT | NEG | 108.43 | 571.35 | L | 1246.51 | 0.09 | 1.74 |
| 10C4-006-026A | MUT | NA | 107.46 | 1171.70 | 139.51 | 546.47 | 0.20 | 3.93 |
| 10C4-006-032A | MUT | NA | 95.40 | 1215.65 | 80.90 | 2000.00 | 0.05 | 0.95 |
| 10C4-006-023A | MUT | NA | 74.64 | 2634.46 | 16.95 | 285.44 | 0.26 | 5.23 |
| 10C4-006-040A | MUT | NEG | 67.00 | 298.40 | L | 197.25 | 0.34 | 6.79 |
| 10C4-006-013A | MUT | NA | 65.51 | 436.81 | L | 338.60 | 0.19 | 3.87 |
| 10C4-006-025A | MUT | NA | 64.59 | 641.69 | L | 319.32 | 0.20 | 4.05 |
| 10C4-006-013B | MUT | NA | 51.70 | 168.69 | L | 134.96 | 0.38 | 7.66 |
| 10C4-006-043A | MUT | NEG | 2.28 | 70.93 | 11.89 | 8.28 | 0.28 | 5.51 |
| 10C4-006-008A | MUT | NEG | 155.50 | 4135.19 | 211.55 | 1234.39 | 0.13 | 2.52 |
| 10C4-006-012A | MUT | NEG | 2.01 | L | L | L | L | L |
| 10C4-006-012C | MUT | NEG | 1.01 | L | L | L | L | L |
| 10C4-006-010A | NA | NA | 170.91 | 1616.76 | 65.54 | 2000.00 | 0.09 | 1.71 |
| 10C4-006-010C | NA | NA | 162.39 | 853.57 | 83.45 | 1878.38 | 0.09 | 1.73 |
| 10C4-006-017A | NA | NA | 109.36 | 313.77 | L | 304.62 | 0.36 | 7.18 |

TABLE 2-continued

Levels of total expression of various analytes and HER1/cMET index.

| Patient No. | EGFR mut | ALK IHC | HER1 | HER2 | HER3 | cMET | HER1/cMET | HER1/cMET index |
|---|---|---|---|---|---|---|---|---|
| 10C4-006-001A | NA | NA | 41.09 | 163.39 | L | 198.91 | 0.21 | 4.13 |
| 10C4-006-005A | NA | NA | 22.53 | 173.32 | L | 301.46 | 0.07 | 1.50 |
| 10C4-006-009A | NA | NA | 22.08 | 209.80 | 14.24 | 36.38 | 0.61 | 12.14 |
| 10C4-006-030A | NA | NEG | 0.97 | L | L | L | | |
| 10C4-006-042A | | | L | L | L | L | | |
| 10C4-006-035A | | | L | L | L | L | | |
| 10C4-006-034A | | | L | L | L | L | | |
| 10C4-006-027A | | | L | L | L | L | | |
| 10C4-006-019C | | | L | L | L | L | | |
| 10C4-006-019A | | | L | L | L | L | | |

Values are in CU per μg of sample. EGFR mut,
EGFR mutation analysis;
ALK IHC; ALK detected by immunohistochemistry;
HER1/cMET, HER1 value divided by cMET value;
HER1/cMET index, HER1/cMET multiplied by 20;
L, below or above detection limit of assay.
The lower/upper limits of detection for the CEER ™ assay are: 2.00/200.00 for HER1, 25.00/2000.00 for HER2, 25.00/200.00 for HER3 and 5.00/2000.00 for cMET.

TABLE 3

Levels of activated expression of various analytes.

| Patient No. | IGF1R | PI3K | CK | pHER1 | pHER2 | pHER3 | pcMET | pIGF1R | pPI3K | pSHC | TKI best response | PFS with EGFR TKI (months) |
|---|---|---|---|---|---|---|---|---|---|---|---|---|
| 10C4-006-006A | 99.05 | 1120.74 | 657.47 | 9.36 | 20.79 | 44.56 | 0.43 | 2.43 | 67.72 | 15.07 | PD | 0.9 |
| 10C4-006-038A | 17.10 | 30.59 | 31.88 | 0.08 | 1.15 | L | L | 1.11 | <4.26 | L | NA | NA |
| 10C4-006-016A | L | 200.26 | 93.98 | 0.18 | 4.19 | 6.66 | L | 2.20 | 11.19 | 3.37 | NA | NA |
| 10C4-006-004A | L | 88.19 | 18.47 | L | L | L | L | L | L | L | PR | 23.4 |
| 10C4-006-046A | 37.21 | 266.55 | 70.79 | 0.18 | L | L | L | 1.63 | >4.26 | L | NA | NA |
| 10C4-006-014B | L | 115.05 | 7.30 | 0.08 | 1.07 | 4.73 | L | 1.78 | 4.73 | 3.52 | PD | 1.4 |
| 10C4-006-014A | 59.56 | 363.69 | 15.61 | 0.08 | 1.06 | 4.88 | L | 1.54 | 3.07 | L | PD | 1.4 |
| 10C4-006-039A | L | 35.09 | 12.73 | 0.07 | 1.24 | L | L | L | <4.26 | L | SD | 0.4 |
| 10C4-006-014C | L | 151.75 | 16.08 | 0.08 | 1.15 | L | L | 2.04 | 2.63 | L | PD | 1.4 |
| 10C4-006-018A | L | 11.87 | 8.48 | 0.11 | 2.40 | 24.27 | 0.30 | 3.95 | 11.31 | L | PD | 0.5 |
| 10C4-006-029A | 35.14 | 821.08 | 1260.55 | 103.90 | 175.2 | 190.84 | 1.34 | 8.06 | 46.90 | 170.26 | PR | 9.3 |
| 10C4-006-031A | L | 222.99 | 84.07 | 0.21 | 2.23 | 15.92 | 0.21 | 2.52 | 6.22 | 7.75 | PR | 10.8 |
| 10C4-006-003A | 57.19 | 72.72 | 36.38 | 0.07 | L | L | L | 1.58 | 1.55 | L | SD | 1.1 |
| 10C4-006-002A | L | 412.10 | 8.43 | 0.13 | 3.41 | L | L | 1.04 | 2.76 | L | PR | 26.2 |
| 10C4-006-028A | 40.73 | 305.08 | 211.66 | 5.62 | 91.72 | 31.61 | 6.12 | 4.48 | 11.11 | 11.85 | NA | NA |
| 10C4-006-037A | 33.40 | 130.18 | 7.44 | 0.12 | 0.95 | 4.10 | L | 0.96 | 2.47 | L | PR | 5.1 |
| 10C4-006-041A | L | 152.75 | 345.10 | 0.51 | 1.55 | 15.19 | L | 0.59 | <4.26 | 1.29 | SD | 2.4 |
| 10C4-006-037C | L | 0.28 | L | 0.06 | 0.62 | L | L | L | <4.26 | L | PR | 5.1 |
| 10C4-006-021A | L | L | L | 0.10 | 1.57 | L | L | 1.95 | 3.60 | L | PR | 25.3 |
| 10C4-006-044A | 73.82 | 425.83 | 296.58 | 0.11 | 1.43 | L | L | 2.31 | L | L | PD | 1 |
| 10C4-006-026A | 140.47 | 1130.98 | 750.60 | 6.06 | 94.21 | 98.34 | 0.85 | 69.35 | 34.39 | 33.48 | PR | 11.2 |
| 10C4-006-032A | 114.10 | 812.99 | 758.13 | 0.33 | 8.69 | 22.42 | 0.86 | 2.32 | 11.34 | 19.32 | PD | 0.5 |
| 10C4-006-023A | L | 98.38 | 70.59 | 0.58 | 24.42 | 27.80 | L | 5.35 | 3.64 | 13.34 | PR | 17.2 |
| 10C4-006-040A | L | 112.33 | 32.01 | 0.04 | L | L | L | L | L | L | PR | 14.4 |
| 10C4-006-013A | L | 111.43 | 3.01 | 0.09 | L | L | L | 1.79 | 3.08 | L | PR | 8.6 |
| 10C4-006-025A | L | 120.39 | 60.75 | 3.60 | 5.36 | 29.11 | 0.28 | 2.57 | 1.97 | 6.87 | PR | 13.7 |
| 10C4-006-013B | L | 61.99 | L | 0.05 | L | L | L | 2.26 | 4.97 | L | PR | 8.6 |
| 10C4-006-043A | L | 23.03 | 117.35 | 0.22 | 13.64 | 8.06 | ND | ND | 11.29 | L | PR | 11.5 |
| 10C4-006-008A | 64.48 | 550.79 | 382.12 | 20.47 | 156.46 | 11.38 | 1.95 | 4.46 | 58.26 | 26.85 | PR | 6.1 |
| 10C4-006-012A | L | 69.92 | L | L | L | L | L | 2.24 | L | L | SD | 5.4 |
| 10C4-006-012C | L | 20.04 | L | L | L | L | L | L | 4.01 | L | SD | 5.4 |
| 10C4-006-010A | 103.75 | 560.86 | 436.57 | 56.21 | 106.31 | 39.63 | 0.71 | 6.38 | 48.93 | 54.02 | PR | 5.1 |
| 10C4-006-010C | 99.68 | 1026.78 | 383.16 | 26.80 | 24.19 | 13.82 | 2.56 | 5.65 | 20.31 | 18.22 | PR | 5.1 |
| 10C4-006-017A | L | 406.86 | 23.66 | 0.09 | L | L | L | 3.35 | 4.35 | 7.98 | PR | 27.1 |
| 10C4-006-001A | L | 47.71 | 10.81 | 0.80 | 9.13 | 175.83 | L | 6.35 | 54.98 | L | NA | NA |
| 10C4-006-005A | L | 29.06 | L | L | L | 131.85 | L | L | 3.32 | L | PD | 0.2 |
| 10C4-006-009A | 82.74 | 597.86 | 411.87 | 0.24 | 5.81 | 29.05 | L | 3.98 | 33.43 | L | PD | 1.8 |
| 10C4-006-030A | L | 6.69 | L | L | L | L | L | L | L | L | SD | 2.1 |
| 10C4-006-042A | L | L | L | 0.04 | L | L | L | 0.58 | <4.26 | L | | |
| 10C4-006-035A | L | L | L | L | L | L | L | L | <4.26 | L | | |
| 10C4-006-034A | L | L | L | L | L | L | L | L | <4.26 | L | | |

TABLE 3-continued

Levels of activated expression of various analytes.

| Patient No. | IGF1R | PI3K | CK | pHER1 | pHER2 | pHER3 | pcMET | pIGF1R | pPI3K | pSHC | TKI best response | PFS with EGFR TKI (months) |
|---|---|---|---|---|---|---|---|---|---|---|---|---|
| 10C4-006-027A | L | L | L | L | L | L | L | L | 2.51 | L | | |
| 10C4-006-019C | L | L | L | L | L | L | L | L | L | L | | |
| 10C4-006-019A | L | L | L | L | L | L | L | L | L | L | | |

Values are in CU per µg of sample.
MUT, mutation;
L, below or above detection limit of assay;
NA, not available;
PD, progressive disease;
PR, partial response to EGFR inhibitor therapy;
SD, stable disease;
PFS, progression free survival.
The lower/upper limits of detection for the CEER™ assay are: 62.60-2000.00 for IGF1R, 25.00/2000.00 for PI3K, 10/2000.00 for CK, 0.33/33.33 for phospho-HER1 (pHER1), 1.70/333.33 for phospho-HER2 (pHER2), 10.67/500.00 for phospho-HER3 (pHER3), 0.33/66.67 for phospho-cMET (pcMET), 1.70/500.00 for phosphor-IGF1R (pIGF1R), 4.17/500.00 for phospho-PI3K (pPI3K), and 4.27/500.00 for phospho-SHC (pSHC).

The measured levels of total and activated HER1 and cMET were compared and transformed into an EGFR/cMET index (Table 2). As shown in FIG. 3A, the EGFR/cMET index was calculated by determining the relative expression of total EGFR to cMET and multiplying the ratio by 20 (e.g., (HER1/cMET)×20). The index was also calculated from the relative expression of phospho-EGFR to phospho-cMET and multiplying the ratio by 20 (e.g., (p-HER1/p-cMET)× 20)

Using retrospective data of the patients, it was determined that the EGFR/cMET index is predictive of the patient's disease status, such as progressive disease, stable disease, partial response, progression-free survival (PFS). The data shows that most patients with progressive disease have a low EGFR/cMET index, such as below a reference cut-off (FIG. 3B).

The correlation plot (FIG. 3A) between PFS versus the EGFR/cMET index across different time points shows that a reduction in the EGFR/cMET index resulted in a worse clinical outcome (e.g., a shorter progression-free survival or progressive disease). The data also shows that patients with a high EGFR/cMET index (above a cut-off) has a better clinical outcome than those with an index below the cut-off. Also, patients with a high index are more likely to benefit from EGFR inhibitor therapy than those with a lower index. Additional plots of PFS versus the EGFR/cMET index (FIGS. 4A and 4B) were generated to determine if there was a difference between patients with or without an activating EGFR mutation.

To further investigate the relationship between progression-free survival and the presence of an activating EGFR mutation, Kaplan-Meier curves were generated according to EGFR mutation status. FIG. 5A shows the Kaplan-Meier curves for all subjects in the study. FIG. 5B shows that patients carrying an EGFR mutation have better PFS compared to those with wildtype EGFR. For instance, about 50% of the patients with an EGFR mutation survived to about 10 months, and 50% of the patients with wildtype EGFR survived to only about 1 month.

Using additional Kaplan Meier curves, the EGFR/cMET cut-off value for the study was established from the data from sample A, such that those patients on EGFR inhibitor therapy with an EGFR/cMET index above the cut-off, had a better PFS than those with an index below the cut-off (FIGS. 6A-C and 7A-C). Reference cut-off values from 1-6 were tested and the data is represented in Table 4. When the ratio cut-off (index cut-off) was set to 6, 6 patients were above the cut-off and also had a better PFS (e.g., a higher percentage of patients survived greater than 8 months), while 23 patients were below the cut-off and few survived greater than 8 months (FIG. 6A). For the patients above the cut-off of 3 (FIG. 7A), about 50% of the patients survived to over 10 months, and for patients below the cut-off, about 50% survived less than 5 months. Table 4 provides a summary of the index cut-off data.

TABLE 4

| EGFR is ___ higher than cMet | EGFR/cMET index cut-off | Above EGFR/cMET Index cut-off (N; number of patients) Below EGFR/cMET Index cut-off (N; number of patients) | Median PFS | p value |
|---|---|---|---|---|
| 100x | 5 | 10 | 12.2 | 0.054 |
| | | 19 | 5 | |
| 80x | 4 | 11 | 12.2 | 0.026 |
| | | 118 | 5 | |
| 60x | 3 | 14 | 11.2 | 0.0001 |
| | | 15 | 1.1 | |
| 40x | 2 | 19 | 9.8 | 0.001 |
| | | 10 | 1.1 | |
| 20x | 1 | 25 | 6.1 | 0.018 |
| | | 4 | 0.1 | |

NSCLC patients with a higher EGFR/cMET index relative to the cut-off of 2 had a superior PFS (e.g., mean PFS of 9.8 months versus 1.1 months) compared to those with an EGFR/cMET index of less than 2 (Table 4). At the cut-off value of 3, patients with higher index value responded to EGFR inhibitor therapy and had a median PFS of 11.2 months, while those with a lower index had a mean PFS of only 1.1 months. Patients with elevated levels of activated cMET expression, and thus lower EGFR/cMET index, exhibited a worse clinical outcome such as a lower PFS (see, Tables 2-4, FIG. 6A-C, FIG. 7A-C). Regardless of EGFR mutation status, the patients with higher levels of EGFR to cMET (or a higher EGFR/cMET index) showed longer PFS (FIGS. 4A and 4B). Thus, the study data shows that a reference cut-off set at 2 can be used to predict whether a patient will experience prolonged PFS (e.g., >1 month) if administered EGFR inhibitor therapy.

Analysis of patients with an EGFR gene mutation revealed that the patients with an EGFR/cMET index of greater than 1 (or an activated EGFR level that is 20-60 times greater than cMET level) can benefit from EGFR inhibitor therapy (FIGS. 8A-C and 9A-C). Patients with an EGFR/cMET index less than 1 are predicted to be resistant to EGFR inhibitor therapy. The data supports the idea that the EGFR/cMET index can predict whether a patient (wild-type or mutant for EGFR) can benefit from EGFR inhibitor therapy.

Figure 7B:
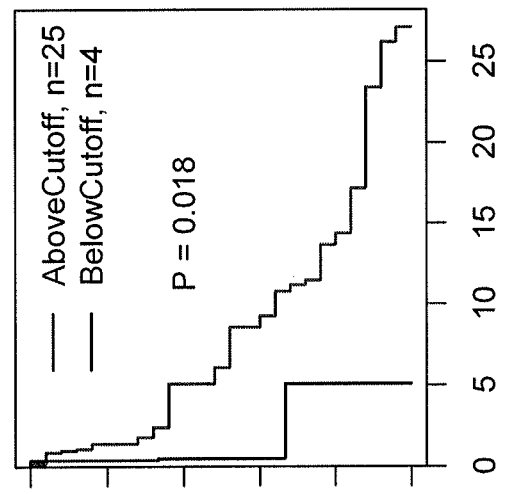
Figure 7C:
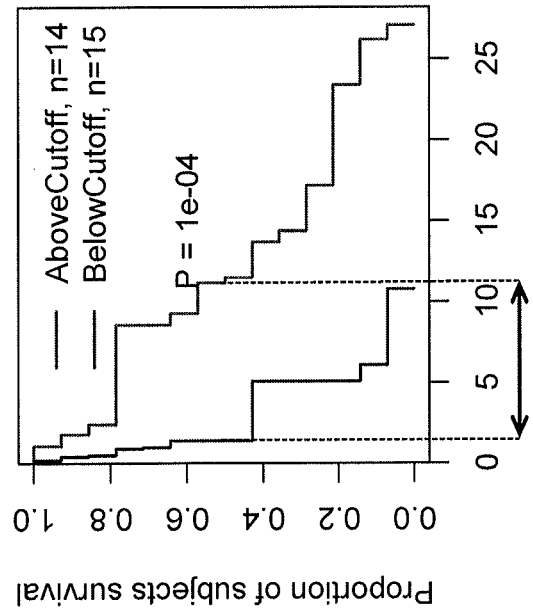
Figure 9A:
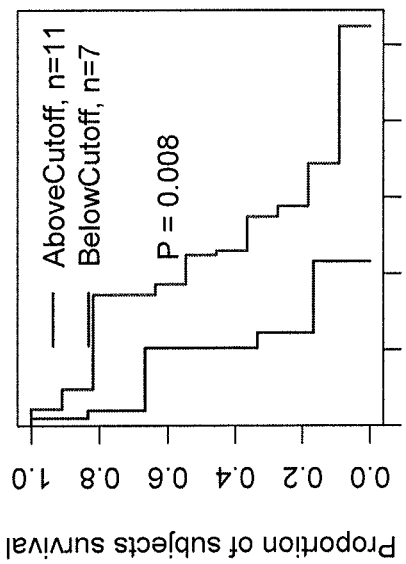
FIGS. 9A-C show more Kaplan-Meier curves of patients with EGFR mutations.
Figure 9B:
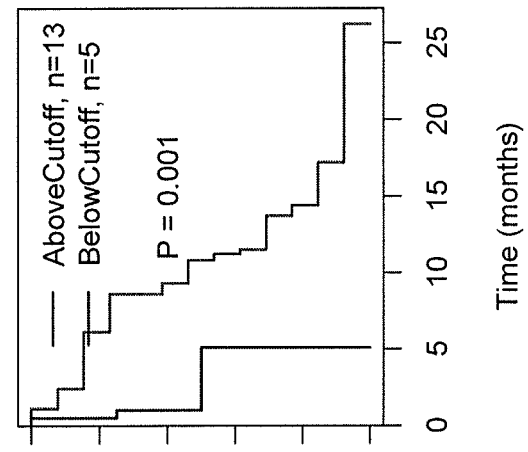
Figure 9C:
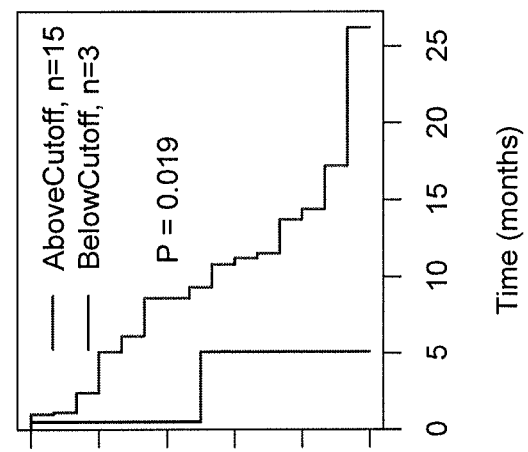

In particular, the study results shows that patients with an EGFR/cMET index of greater than 2 (or an activated EGFR level is 40-120 times higher than cMET level) can benefit from EGFR inhibitor therapy (FIG. 6A-C). The results also showed that patients with an EGFR/cMET index of less than 2, can benefit from cMET inhibitor therapy or cMET inhibitor therapy in combination with EGFR inhibitor therapy (FIG. 7A-C). Patients with an EGFR/cMET index below the ratio cutoff of 2 are predicted to have a significantly shorter duration of PFS compared to those patients with an EGFR/cMET index above the cut-off.

Figure 10:
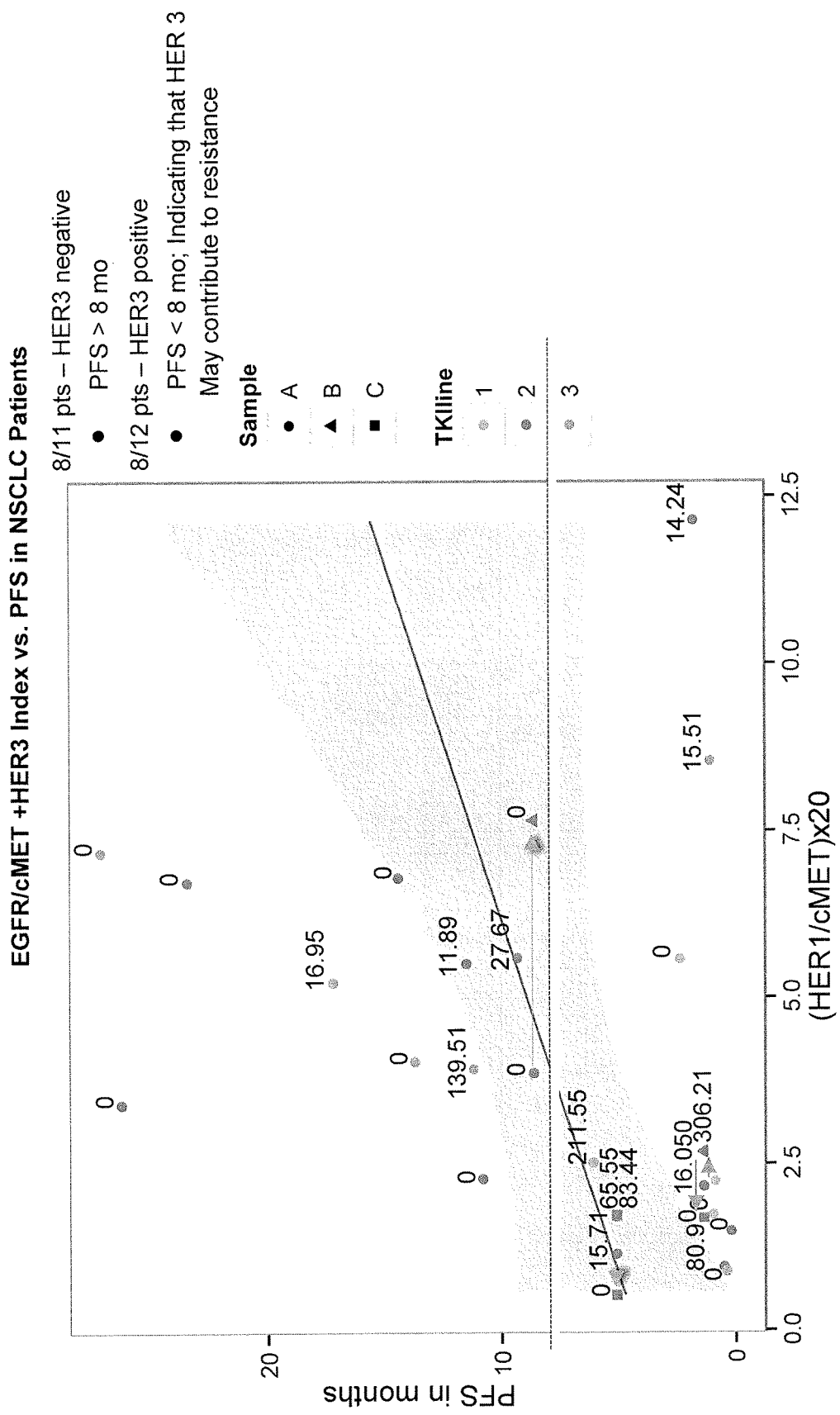
FIG. 10 shows a correlative plot of PFS and the EGFR/cMET index of NSCLC patients in the study. The data shows that relative increases in cMET level over time (or a reduction in the EGFR/cMET index over time) lead to poorer PFS (e.g, shorter PFS).

The study also determined that patients with shorter PFS (<8 months) had significantly higher levels of total and phosphorylated HER3 (67% positive) than patients with longer PFS (>8 months, 27% positive). See, FIG. 10. 8 out of 11 patients who had a PFS of >8 months were determined to be HER3 negative and 8 out of 12 patients who had a PFS of <8 months were HER3 positive. The data indicated that higher levels of total and phosphorylated HER3 can contribute to EGFR inhibitor resistance. FIG. 10 shows that as relative cMET level increased (reduction of activated EGFR/cMET index) during the course of EGFR treatment, PFS decreased (shortened or worsened). Longitudinally collected FNA specimen comparison provided evidence of a feedback loop causing compensatory crosstalk via cMET activation, which led to disease progression.

Detailed analysis of Patient #10. Patient #10 (samples 10C-4-006-10A and 10C-4-006-10C in Table 2 and 3) received a treatment course of gefitinib, exhibited partial response and relapsed after 5.1 months. Sample A was taken from Patient #10 prior to receiving gefitinib ($t_1$) and Sample C after the completion of the treatment course during relapse ($t_2$; 10C-4-006-10A and 10C-4-006-10C, respectively). The CEER assay detected very high levels of total HER1 expression and activated HER1 expression in Sample A. During the course of therapy Patient #10 showed partial response and a reduction of phospho HER1, HER2, and HER3 in Sample C. Phospho-cMET level were elevated at the later time point and the index was lower compared to the earlier time point. Thus, the index indicates that the patient would benefit from receiving cMET inhibitor therapy. The data clearly demonstrates that activated cMET plays a critical role in resistance to EGFR inhibitor treatment.

Conclusions: The results of the study show that the EGFR/cMET index can be used to predict a patient's sensitivity (or response) to EGFR inhibitor therapy, cMET inhibitor therapy, or EGFR inhibitor and cMET inhibitor therapy. In addition, the data demonstrates that increased levels of cMET correlate with resistance to EGFR tyrosine kinase inhibitors. The data also shows that the presence of activated HER3 may correlate with drug resistance. This example illustrates that the EGFR/cMET index and the level of activated signaling analytes such as activated cMET and HER3 can serve as predictive markers for selecting of an effective therapy for the treatment of NSCLC.

Example 2

Measuring cMET Using a cMET Homodimer CEER™ Assay or a cMET:PI3K CEER™ Assay

The cMET homodimer CEER™ assay was used for detecting the level of cMET homodimer in a cellular extract of tumor cells. The assay comprised of: (1) a capture antibody specific to phospho-cMET; (2) a detection antibody which detects the total amount of the analyte (i.e., activation state-independent antibody); and (3) a detection antibody which detects the total amount of the analyte (i.e., activation state-independent antibody) but recognizes a different epitope than detection antibody (FIG. 12A). The data demonstrates that cMET homodimer was detected in a sample containing as few as 30 cells (FIGS. 12B and C).

The cMET:PI3K CEER™ assay was used for detecting the level of cMET:PI3K complex in a cellular extract of tumor cells. The assay comprised of: (1) a capture antibody specific to PI3K; (2) a detection antibody which detects the total amount of the analyte (i.e., activation state-independent antibody); and (3) a detection antibody which detects the total amount of the analyte (i.e., activation state-independent antibody) but recognizes a different epitope than detection antibody (FIG. 13A). The date shows that cMET:PI3K complex was detected in a sample containing 300 cells (FIGS. 13 B and C).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for administering an anticancer drug to a non-small cell lung cancer (NSCLC) subject and longitudinally monitoring the subject receiving the anticancer drug, the method comprising:
   (a) detecting and/or quantifying the expression level and/or activation level of HER1 in a cellular extract produced from an isolated cancer cell from the subject;
   (b) detecting and/or quantifying the expression level and/or activation level of cMet in a cellular extract produced from an isolated cancer cell from the subject;
   (c) determining a HER1/cMET index by dividing the expression level of HER1 by the expression level of c-MET or by dividing the activation level of HER1 by the activation level of cMET multiplied by a numerical factor of 20 in the cellular extracts at time point 1 ($t_1$), wherein the HER1/c-MET index is between 0-20;
   (d) administering an EGFR inhibitor when the HER1/c-MET index is between 2 and 20, or when the HER1/c-MET index is between 0 and 1.9 administering a c-MET inhibitor or a combination of a c-MET inhibitor and an EGFR inhibitor;
   (e) repeating steps (a) and (b) to determine a HER1/cMET index later in time based on the expression levels of HER1 and c-Met analytes in the cellular extracts at time point 2 ($t_2$);
   (f) comparing the HER1/cMET index of the earlier time point ($t_1$) to the HER1/cMET index at the later time point ($t_2$), to monitor the subject receiving the anticancer drug; and
   (g) continuing administering or selecting a suitable anticancer drug(s) to the subject based upon a change in the HER1/cMET index.

2. The method of claim 1, wherein an HER1/cMET index at $t_2$ that is greater than at $t_1$ indicates prolonged progression-free survival (PFS) for the subject.

3. The method of claim 1, wherein an HER1/cMET index at $t_2$ that is less than at $t_1$ indicates shortened PFS for the subject.

4. The method of claim 1, wherein the expression levels of EGFR and cMet are used in calculating the HER1/c-MET index.

5. The method of claim 1, wherein the activation levels of EGFR and cMet are used in calculating the HER1/c-MET index.

6. The method of claim 1, wherein the expression levels and/or activation levels of HER1 and cMET are determined by a multiplex high-throughput assay.

7. The method of claim 1, wherein the expression levels of HER1 and cMet are determined by mRNA levels.

8. The method of claim 7, wherein the mRNA levels are measured using Northern blotting, Reverse Transcriptase Polymerase Chain Reaction (RT-PCR), or quantitative RT-PCR (qRT-PCR).

9. The method of claim 1, wherein an HER1/cMET index at $t_2$ that is less than at $t_1$ indicates resistance to EGFR inhibitor therapy.

10. The method of claim 1, wherein a HER1 mutation indicates a better progression-free survival rate compared to wild type HER1.

11. The method of claim 10, wherein the EGFR mutation is selected from the group consisting of E709D, E709Q, E709K, E709A, E709A, G719S, G719C, G719A, G719R, S768I, T790M, L858R, L858M, L861Q and L861R.

12. The method of claim 9, wherein a cMet inhibitor is included in the therapy for the subject.

13. The method of claim 1, wherein the HER1/c-MET index at $t_2$ is between 0-20.

14. The method of claim 13, wherein when the HER1/c-MET index is between 2 and 10, the subject is administered an EGFR inhibitor.

15. The method of claim 14, wherein the EGFR inhibitor is selected from the group consisting of Cetaximab, Panitumumab, Matuzumab, Nimotuzumab, ErbB1 vaccine, Erlotinib, Gefitinib, EKB 569, CL-387-785 and a combination thereof.

16. The method of claim 9, wherein when the HER1/c-MET index is between 1 and 1.9, the subject is administered a cMET inhibitor or a combination of a cMET inhibitor and an EGFR inhibitor.

17. The method of claim 16, wherein the c-MET inhibitor is selected from the group consisting of MAG102 and MetMab, ARQ197, XL184, PF-02341066, GSK1363089/XL880, MP470, MGCD265, SGX523, PF04217903 JNJ38877605, INCB28060, AMG-458, E7050, MK-2461, BMS-777607 and a combination thereof.

18. The method of claim 1, wherein a higher level of pHER3 at $t_2$ compared to $t_1$ indicates resistance to EGFR inhibitor therapy.

19. The method of claim 1, wherein determining and/or quantifying the expression of HGF is used as a surrogate for the expression of cMET.

* * * * *